US012714873B1

(12) United States Patent
Otsubo

(10) Patent No.: US 12,714,873 B1
(45) Date of Patent: Aug. 25, 2026

(54) REPELLING MAGNET ASSEMBLY

(71) Applicant: Hirofusa Otsubo, Middle Village, NY (US)

(72) Inventor: Hirofusa Otsubo, Middle Village, NY (US)

( * ) Notice: Subject to any disclaimer, the term of this patent is extended or adjusted under 35 U.S.C. 154(b) by 459 days.

(21) Appl. No.: 18/511,431

(22) Filed: Nov. 16, 2023

Related U.S. Application Data

(63) Continuation-in-part of application No. 17/896,266, filed on Aug. 26, 2022, now abandoned.

(51) Int. Cl.
*A61N 2/06* (2006.01)
*C02F 1/48* (2023.01)
*H01F 7/02* (2006.01)

(52) U.S. Cl.
CPC ................ *A61N 2/06* (2013.01); *C02F 1/481* (2013.01); *H01F 7/021* (2013.01); *H01F 7/0221* (2013.01)

(58) Field of Classification Search
CPC . A61N 2/06; C02F 1/481; H01F 7/021; H01F 7/0221
See application file for complete search history.

(56) References Cited

U.S. PATENT DOCUMENTS 4,367,143 A * 1/1983 Carpenter ............ B03C 1/0332 210/222
4,888,113 A * 12/1989 Holcomb ................ C02F 1/485 210/695
4,946,590 A * 8/1990 Hertzog ................ B03C 1/0332 210/232
6,544,164 B1 4/2003 Fan
6,864,773 B2 3/2005 Perrin
7,371,472 B2 5/2008 Fukuda
11,610,731 B2 3/2023 Otsubo
2004/0104320 A1 6/2004 Exler
2004/0108789 A1 6/2004 Marshall
2005/0148809 A1 7/2005 Delaney
2008/0128429 A1 6/2008 Towery et al.
2013/0048827 A1 2/2013 Meier et al.
2013/0125584 A1 5/2013 Huynh
2015/0359301 A1 12/2015 Lavorato et al.

(Continued)

FOREIGN PATENT DOCUMENTS

WO WO 2022191928 9/2022

OTHER PUBLICATIONS

Written Opinion of the International Searching Authority for PCT/US 22/45087 established by the ISA/US completed on Jan. 3, 2023.

(Continued)

*Primary Examiner* — Waqaas Ali
(74) *Attorney, Agent, or Firm* — Goldstein Law Offices, P.C.

(57) ABSTRACT

A detachable repelling magnet assembly for use with a water pipe, comprising a plurality of magnetic components positioned in a repelling sequence in which each magnetic component exerts a repelling force against the magnetic component adjacent thereto, the magnetic components are disposed linearly within a flexible outer casing secured in linear alignment with the water pipe, or are disposed in opposing pairs within a housing formed of a first portion and a second portion which fit together to circumferentially enclose a portion of the water pipe.

15 Claims, 21 Drawing Sheets

(56) References Cited

U.S. PATENT DOCUMENTS

| | | | |
|---|---|---|---|
| 2016/0194105 | A1 | 7/2016 | Springer |
| 2020/0143964 | A1 | 5/2020 | Meng et al. |
| 2021/0170189 | A1 | 6/2021 | Souder |
| 2022/0060097 | A1 | 2/2022 | Konno et al. |

OTHER PUBLICATIONS

International Preliminary Report on Patentability of the International Preliminary Examining Authority for PCT/US 22/45087 established by the IPEA/US completed on Jan. 3, 2023.

* cited by examiner

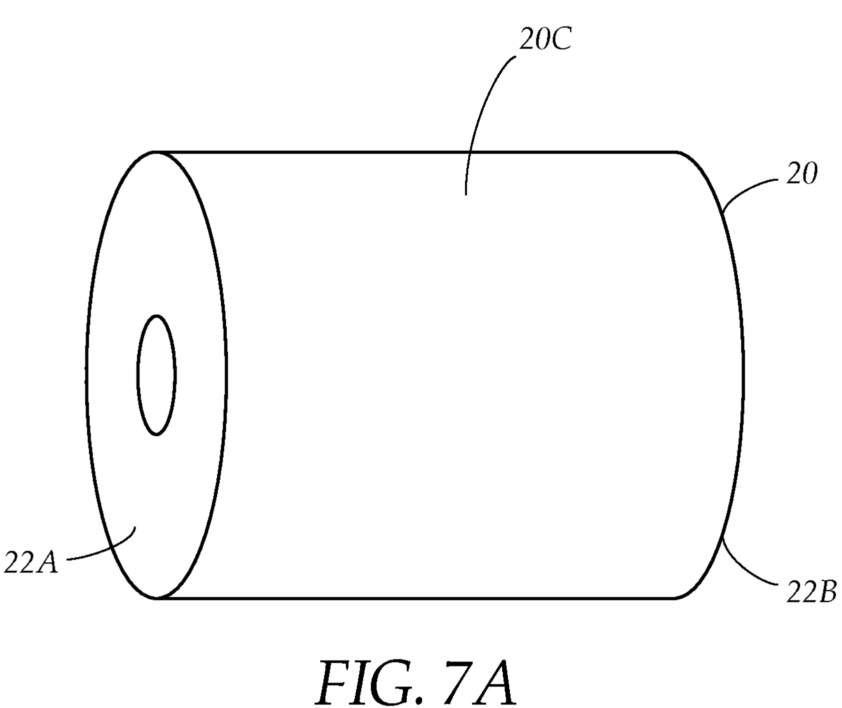
FIG. 7A
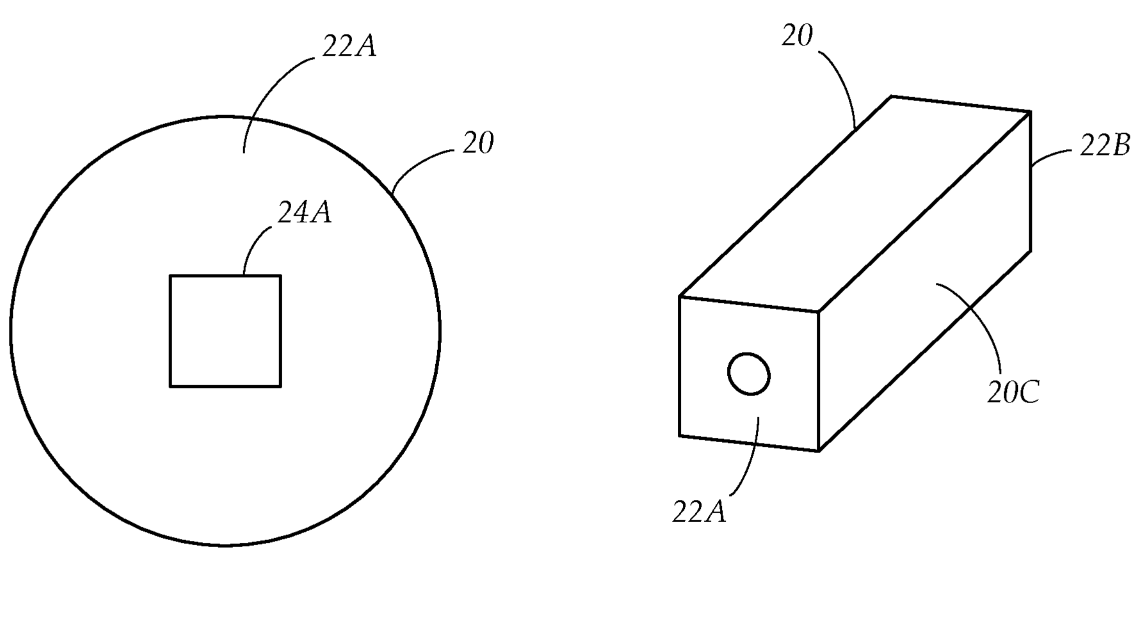
FIG. 7B
FIG. 7C

REPELLING MAGNET ASSEMBLY

CROSS-REFERENCE TO RELATED APPLICATIONS

This application is a continuation in part of patent application Ser. No. 17/896,266 filed in the United States Patent Office on Aug. 26, 2022, claims priority therefrom, and is expressly incorporated herein by reference in its entirety.

TECHNICAL FIELD

The present disclosure relates generally to a magnetic therapeutic device. More particularly, the present disclosure relates to an apparatus containing a sequence of magnetic components held together in a repelling configuration, which can be configured as a wearable device to be worn on the body, or be attached to a water pipe to raise the pH levels of the water towards alkalinity.

BACKGROUND

Magnets are commonly used to provide homeopathic treatments for chronic disease. Magnetic fields induce electrons to flow in a negatively charged wave and have been demonstrated to raise pH levels in water towards alkalinity. Magnetic fields can therefore influence the flow of free electrons to alter voltage potential within cells of the human body and stimulate healing.

Many magnetic therapeutic devices can be found within the prior art, particularly wearable devices which are held in close proximity to or against the body. Many such devices contain magnets linked together by magnetic attraction. However, magnetic attraction causes magnetic force lines to flow between magnets, thus narrowing areas around the device where magnetic exposure is possible. Other devices employ a spread of standard magnets which project unaltered magnetic fields which flow from pole to pole. These devices do not provide sufficient magnetic exposure, and the resulting magnetic fields are weak.

However, the devices within the prior art do not employ magnets placed in a repelling configuration in which the magnetic fields are redirected outwardly away from a magnetic axis by repelling magnetic forces. Such an arrangement would widen the areas around a device in which magnetic exposure is possible, and would further strengthen the magnetic repelling forces produced by placing repelling magnets in very close proximity with each other.

In contrast to the devices within the prior art, repelling magnets can be used to apply fundamental principles of quantum medicine to promote health and healing by altering the voltage potential within human cells. It is commonly known that two properly configured magnets placed in a repelling position will create a demagnetization effect resulting in a significant reduction of magnetic strength caused by the collision of repelling magnetic fields. The collision of repelling magnetic fields alters the directional flow of electrons from pole to pole within the magnetic fields and dislodges some of the electrons from their normal flow, turning them into free electrons. Furthermore, these free electrons are non-directional, creating a scalar field of energy just like gravity. Positioning repelling magnets near the human body thus exposes the body to a supply of free electrons which act as electron donors to restore the pH of the body to a healthy level of alkalinity. Similarly, repelling magnets can be placed adjacent to or surrounding a water pipe or hose, thus increasing the pH of the water flowing through the pipe or hose by exposure to the free electrons produced by the repelling magnets.

Therefore, there is a clear and unfulfilled need for a new wearable magnetic device which employs a dense array of repelling magnets to produce strong repelling forces which increase exposure of free electrons to a wearer, thus enhancing the beneficial effects of magnetic therapy according to the principles of quantum medicine. Furthermore, the array of repelling magnets can also be placed within a casing or housing which allows the device to be attached to water pipes and hoses to produce a steady source of alkaline water.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a wearable magnetic apparatus for exposing a wearer to free electrons. Accordingly, the present disclosure provides a repelling magnetic assembly comprising a plurality of magnetic components and a retaining member. Each magnetic component has a channel and projects a magnetic field, and the retaining member extends through the channels of the magnetic components to form a physical linkage therebetween. Furthermore, the retaining member may be formed as a loop or segment which can be placed in close proximity to a wearer's body or around a portion thereof.

It is an aspect of an example embodiment in the present disclosure to provide a wearable magnetic apparatus which projects a concentration of magnetic fields which project outwardly to increase magnetic exposure. Accordingly, the plurality of magnetic components form a repelling sequence disposed along the retaining member in which each of the magnetic components exerts a magnetic repelling force against each magnetic component adjacent to it within the repelling sequence. Furthermore, the repelling forces act upon the magnetic fields to spread and redirect the magnetic force lines outwardly away from a magnetic axis, thus increasing magnetic exposure to the wearer.

It is a further aspect of an example embodiment in the present disclosure to provide a wearable magnetic apparatus which increases the redirection of the magnetic field by strengthening the repelling forces. The strength of the magnetic repelling force is inversely proportional to the separation interval between two repelling magnets. Accordingly, the repelling sequence can be formed using a plurality of alternate magnetic components each comprising two repelling magnetic subcomponents forced together in physical contact, thus minimizing the separation interval. Direct physical contact between the two magnetic subcomponents is maintained using a bonding means such as a bonding adhesive, or by encasing the two magnetic subcomponents within a containing shell.

It is yet a further aspect of an example embodiment in the present disclosure to provide a detachable repelling magnet assembly which can be attached to a water pipe to expose water within the water pipe to the magnetic fields produced by the magnetic components. Accordingly, the present disclosure provides an outer casing adapted to enclose a repelling sequence of magnetic components. The outer casing is fastened to the water pipe in linear alignment therewith. The present disclosure also provides a detachable repelling magnet housing formed of a first portion and a second portion, the first portion and the second portion are adapted to fit together in an abutting position to circumferentially grip the water pipe. The first portion and the second portion each contain a magnetic component, and the magnetic components form an opposing pair which exert a repelling force therebetween. The housing further comprises one or more fasteners which secure the first portion and the second portion together in the abutting position by overcoming the repelling force.

The present disclosure addresses at least one of the foregoing disadvantages and solutions. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

FIG. 7A is a diagrammatical perspective view of a variant of the magnetic component configured as an elongated cylinder, in accordance with an embodiment in the present disclosure.

FIG. 7B is a diagrammatical front view of a variant of the magnetic component with the channel opening in a rectangular configuration, in accordance with an embodiment in the present disclosure.

FIG. 7C is a diagrammatical perspective view of a variant of the magnetic component configured as a rectangular prism, in accordance with an embodiment in the present disclosure.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 1A:
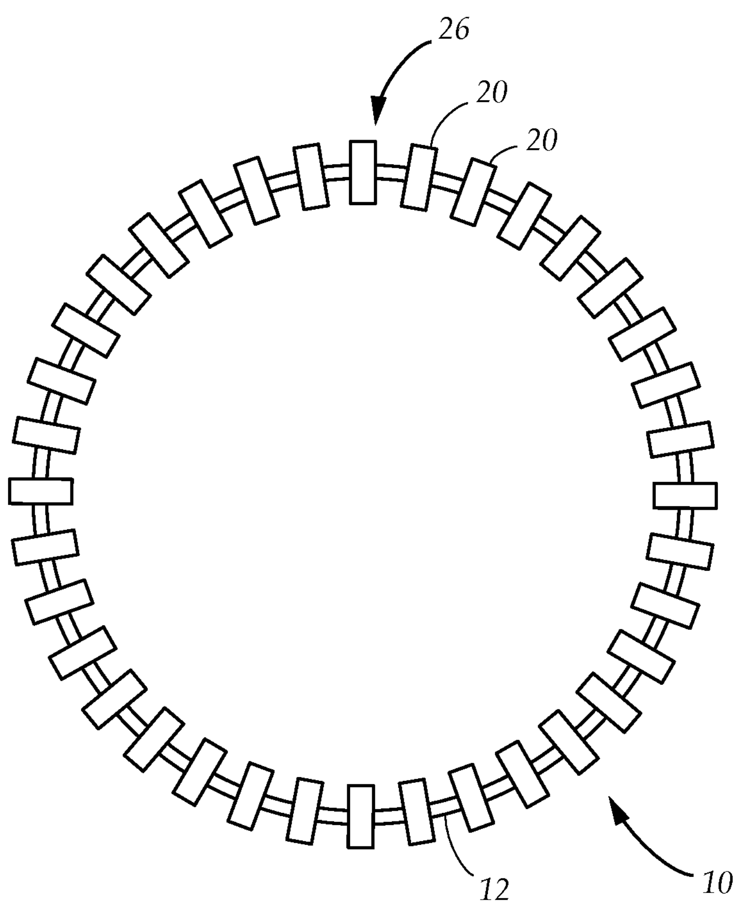
FIG. 1A is a diagrammatical top view of a repelling magnet assembly containing a repelling sequence of magnetic components held together in a repelling configuration by a retaining member, in accordance with an embodiment in the present disclosure.
Figure 1B:
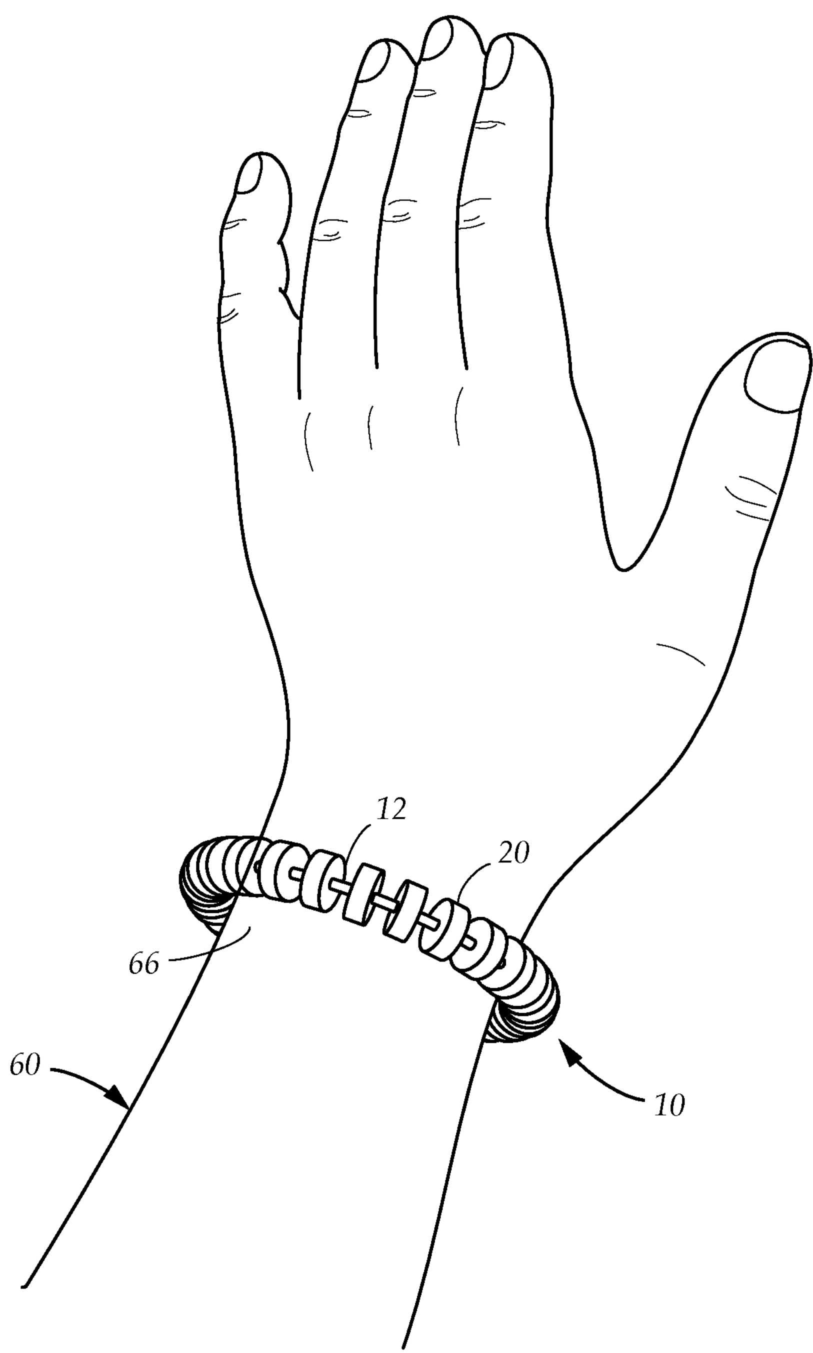
FIG. 1B is a diagrammatical perspective view of the repelling magnet assembly being worn around a wearer's wrist, in accordance with an embodiment in the present disclosure.

FIGS. 1A-B illustrate a repelling magnet assembly 10 comprising a retaining member 12 and a plurality of magnetic components 20. The plurality of magnetic components 20 are arranged in a repelling sequence 26 comprising at least two of the magnetic components 20 disposed in a linear fashion, in which each of the magnetic components 20 magnetically repels the magnetic components 20 adjacent thereto. Each of the magnetic components 20 is secured within the repelling sequence 26 by the retaining member 12. By varying the structure and shape of the retaining member 12, the repelling magnet assembly 10 may be implemented in a variety of configurations which allow it to be worn by a wearer 60. As contemplated in various embodiments, the repelling magnet assembly 10 may be placed adjacent to or in close proximity to the wearer's 60 body, or be wrapped around a portion of the body. For example, the retaining member 12 may be configured as a loop which allows the repelling magnet assembly 10 to be worn around the wrist 66 of the wearer 60.

Figure 2A:
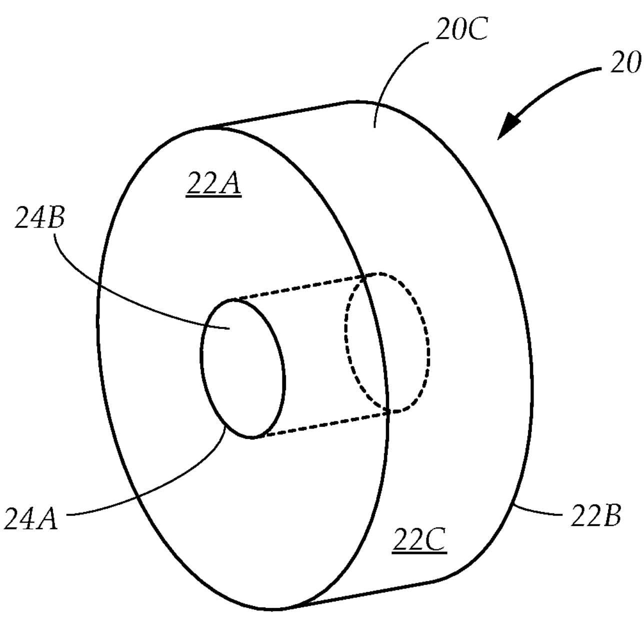
FIG. 2A is diagrammatical perspective view of one of the magnetic components, showing a channel which passes between a component first face and a component second face of the magnetic component, in accordance with an embodiment in the present disclosure.
Figure 2B:
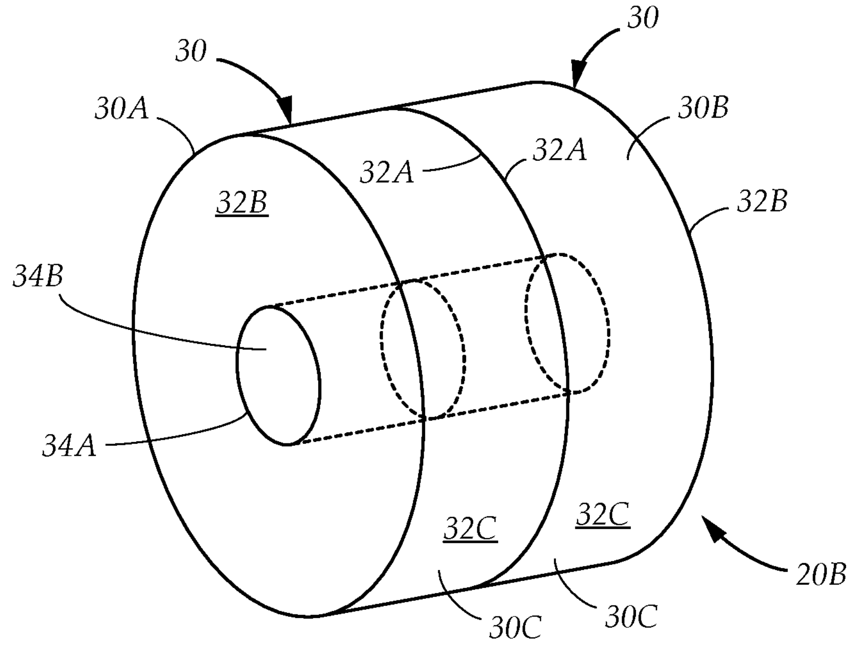
FIG. 2B is a diagrammatical perspective view of an alternative magnetic component formed of two magnetic subcomponents affixed together in the repelling configuration, in accordance with an embodiment in the present disclosure.

Referring to FIG. 2A while continuing to refer to FIGS. 1A-B, each magnetic component 20 has a component first face 22A, a component second face 22B oriented distally in relation to the component first face 22B, and a component body 20C which extends between the component first face 22A and the component second face 22B. Each magnetic component 20 contains ferromagnetic metals such as iron, cobalt, nickel, or rare earth metals, an may be configured in a variety of shapes. For example, the magnetic component 20 may be configured as a disc with the component body 20C having a cylindrical component outer surface 22C extending between the component first face 22A and the component second face 22B. In one embodiment, the component first face 22A and the component second face 22B are substantially flat and are disposed in a transverse manner in relation to the component outer surface 20C.

Each magnetic component 20 has a pair of channel openings 24A positioned on the component first face 22A and the component second face 22B, and a channel 24B which passes through the component body 20C between the pair of channel openings 24A. In a preferred embodiment, the channel openings 24A are disposed centrally upon the component first face 22A and the component second face 22B, and the channel 24B passes longitudinally though the component body 20C.

Figures 3A, 3B:
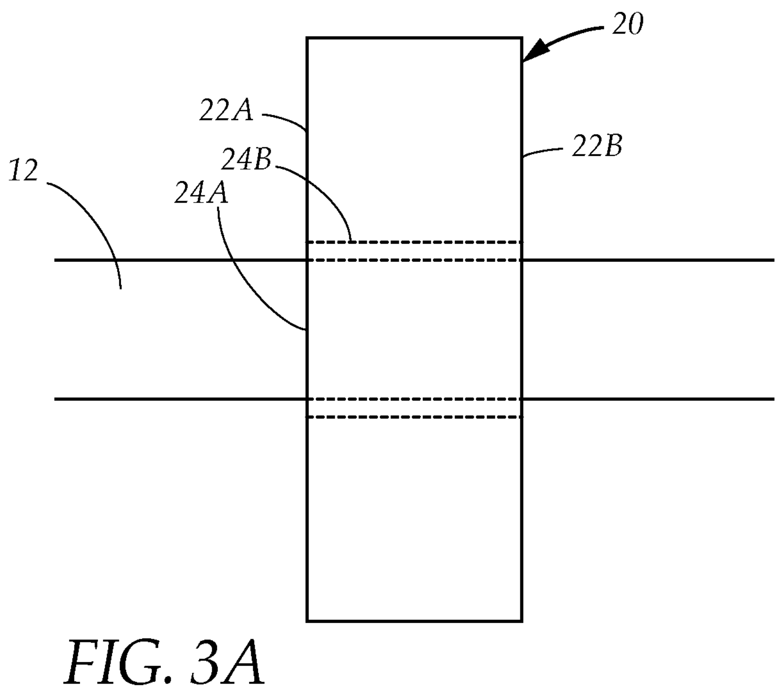
FIG. 3A is a side sectional view of the retaining member passing through the channel of one of the magnetic components, in accordance with an embodiment in the present disclosure.
FIG. 3B is a side view of a repelling sequence of magnetic components oriented in a repelling configuration, where magnetic repelling forces maintain separation intervals between each of the magnetic components within the repelling sequence, in accordance with an embodiment in the present disclosure.
Figure 6A:
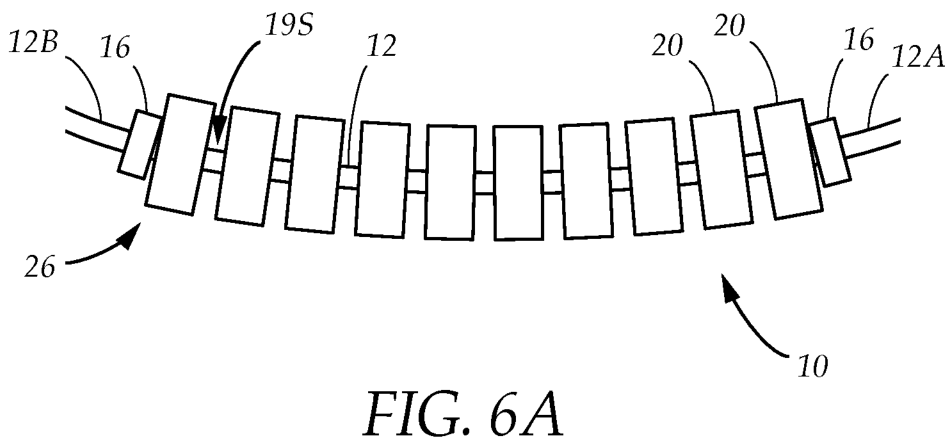
FIG. 6A is a diagrammatical depiction of a variation of the repelling magnet assembly in a segment configuration where the magnetic components are positioned between a first end and a second end of the retaining member, in accordance with an embodiment in the present disclosure.
Figure 6B:
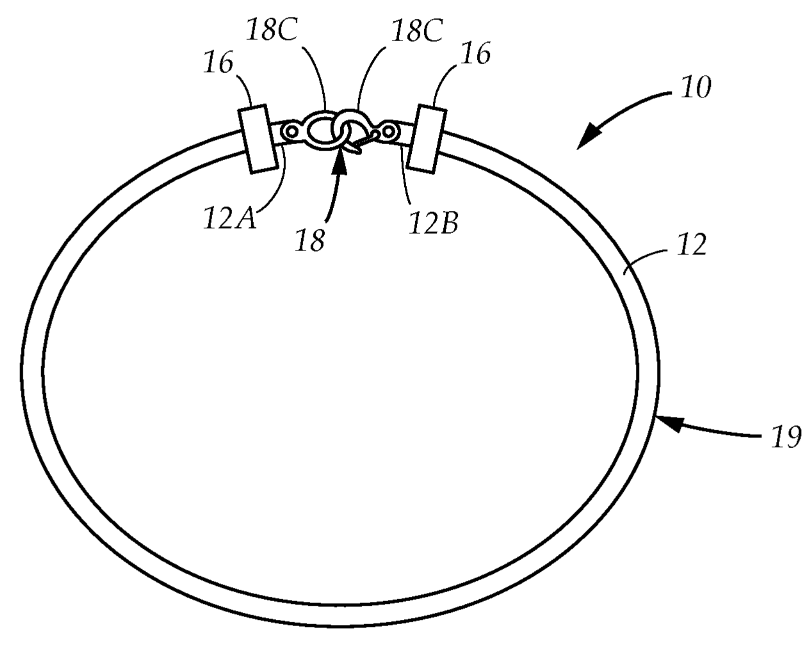
FIG. 6B is a diagrammatical top view of a variation of the retaining member configured with a fastener which allows the first end and the second end to be detachably fastened therebetween, in accordance with an embodiment in the present disclosure.

Referring to FIG. 3A while also referring to FIG. 1A and FIGS. 6A-B, the retaining member 12 provides a physical linkage which secures each of the magnetic components 20 within the repelling sequence 26. In a preferred embodiment, the retaining member 12 has a length and a width, with the length being substantially greater than the width. For example, the retaining member 12 may be formed as a rod, a wire, a chain, a tube, or other structure in which the length of the structure greatly exceeds the width. In turn, the width of the retaining member 12 is narrower than a diameter of the channel opening 24A and the channel 24B of each of the magnetic components 20. The retaining member 12 passes longitudinally through the channel 24B of each of the magnetic components 20 within the repelling sequence 26.

Turning to FIGS. 3A-B, FIG. 4A, and FIG. 4C while also referring to FIG. 1A and FIG. 2A, each magnetic component 20 projects a magnetic field 40. The magnetic components 20 within the repelling sequence 26 are disposed in a repelling configuration, in which each of the magnetic components 20 exerts a magnetic repelling force 44 against the magnetic components 20 adjacent thereto and creates a separation interval 28 between each of the magnetic components 20 within the repelling sequence 26. In a preferred embodiment, the repelling force 44 is sufficient to prevent the magnetic components 20 from sliding or being displaced along the retaining member 12 when exposed to moderate physical force, thus avoiding the need to physically adhere or bond the channel 24B to the retaining member 12.

In one embodiment, each magnetic component 20 has a first magnetic pole 46A oriented with the component first face 22A and a second magnetic pole 46B oriented with the component second face 22B. Each magnetic component 20 may have a magnetic axis 48 which extends longitudinally between the component first face 22A and the component second face 22B and which may be approximately coaxial with the channel 24B. The first magnetic pole 46A and the second magnetic pole 46B have opposite magnetic polarities. Opposite magnetic polarities will cause a magnetic attractive force to be exerted, whereas like magnetic polarities will cause a repelling force 44 to be exerted. For illustrative purposes, the first magnetic pole 46A may correspond to the north pole, while the second magnetic pole 46B may correspond to the south pole.

The repelling configuration ensures that each magnetic component 20 within the repelling sequence 26 will exert a repelling force 44 against each magnetic component 20 to which it is adjacent. In one embodiment, the magnetic components 20 are arranged such that the component first face 22A of each magnetic component 20 is oriented towards the component first face 22A of the magnetic component adjacent thereto. Conversely, the component second face 22B of each magnetic component 20 is oriented towards the component second face 22B of the adjoining magnetic component 20.

For illustrative purposes, an example repelling sequence 26 shown in FIG. 3B comprises four magnetic components 20. Proceeding from left to right, the first and second magnetic components 20 are arranged such that the component first face 22A and the first magnetic pole 46A of the first magnetic component 20 is oriented towards the component first face 22A and the first magnetic pole 46A of the second magnetic component. Continuing down the repelling sequence 26, the second and third magnetic components 20 are arranged such that the component second face 22B and the second magnetic pole 46B of the second and third magnetic components are oriented towards each other. Lastly, the fourth magnetic component 20 is oriented such that the component first face 22A and the first magnetic pole 46A of the fourth magnetic component 20 is oriented towards the component first face 22A and the first magnetic pole 46A of the third magnetic component 20.

Figure 4A:
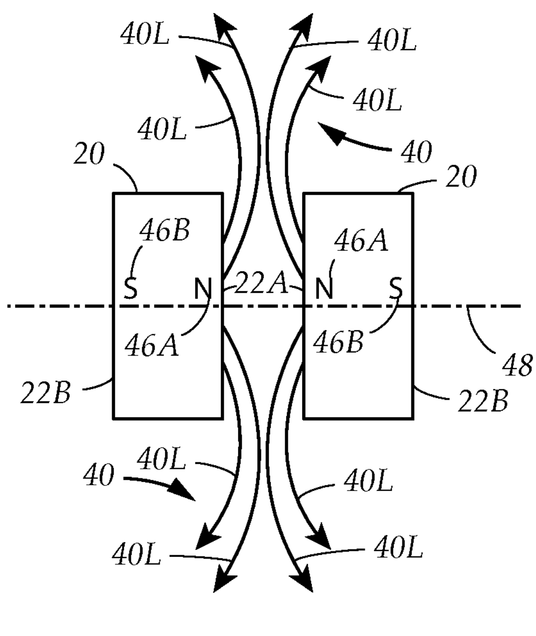
FIG. 4A is a diagrammatical depiction of the magnetic fields projected by two magnetic components oriented in the repelling configuration, the magnetic fields are depicted using field lines, in accordance with an embodiment in the present disclosure.

Turning to FIG. 4A while also referring to FIG. 3B, the magnetic fields 40 are represented through magnetic field lines 40L which flow from the first magnetic pole 46A of each magnetic component 20 toward the second magnetic pole 46B. Where an attracting force is exerted between two adjoining magnets, a portion of the magnetic field lines 40L would flow towards the adjoining magnetic poles of opposite polarity. However, when magnetic poles of like polarity are placed in adjoining proximity, the magnetic fields 40 emitted by each magnetic component 20 will repel the magnetic field 40 of the adjacent magnetic component 20. The magnetic field 40 of each magnetic component 20 will be repelled away from the adjacent magnetic component 20, causing the magnetic field lines 40L to flow outwardly away from the magnetic axis 48. The repelling configuration therefore widens and disperses the magnetic fields 40 of the magnetic components 20 within the repelling sequence 26.

Figure 4B:
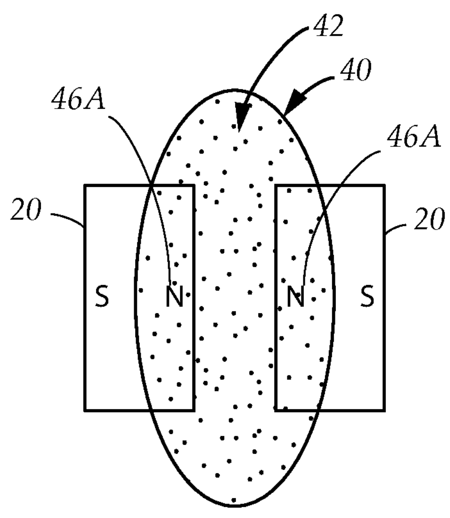
FIG. 4B is a diagrammatical depiction of the magnetic fields of the two magnetic components influencing free electrons present within the magnetic fields, in accordance with an embodiment in the present disclosure.
Figure 4C:
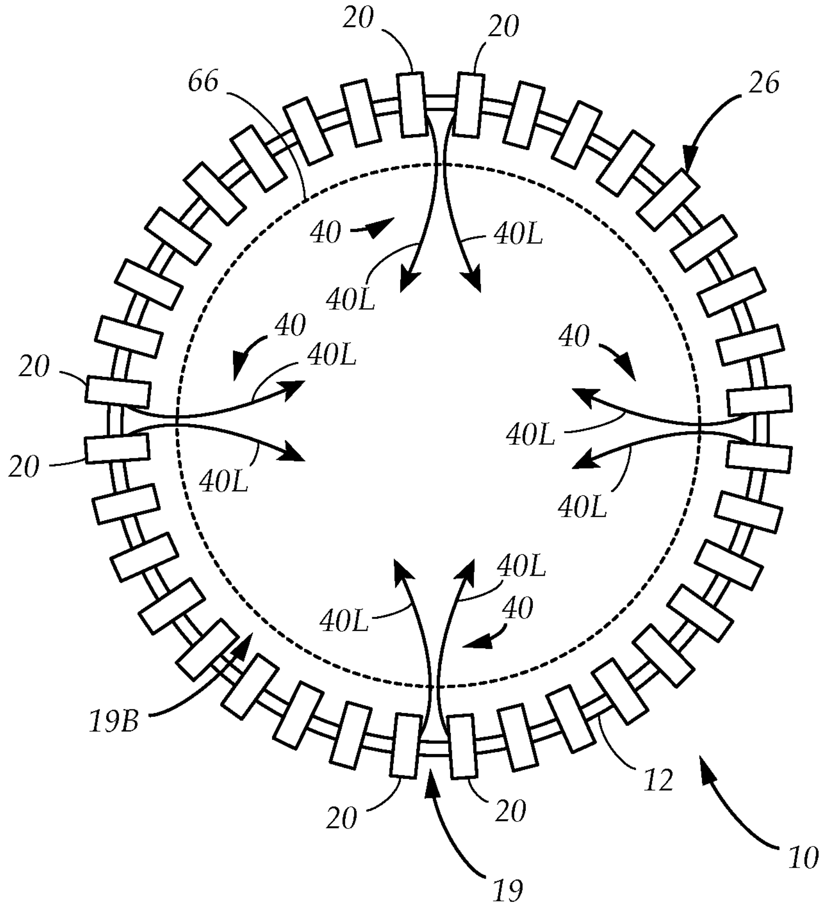
FIG. 4C is a diagrammatical top view of the repelling magnetic assembly worn around a representation of the wrist, further showing the magnetic field lines flowing into a loop interior space resulting from the repelling forces exerted by the magnetic fields of the magnetic components, in accordance with an embodiment in the present disclosure.
Figure 5A:
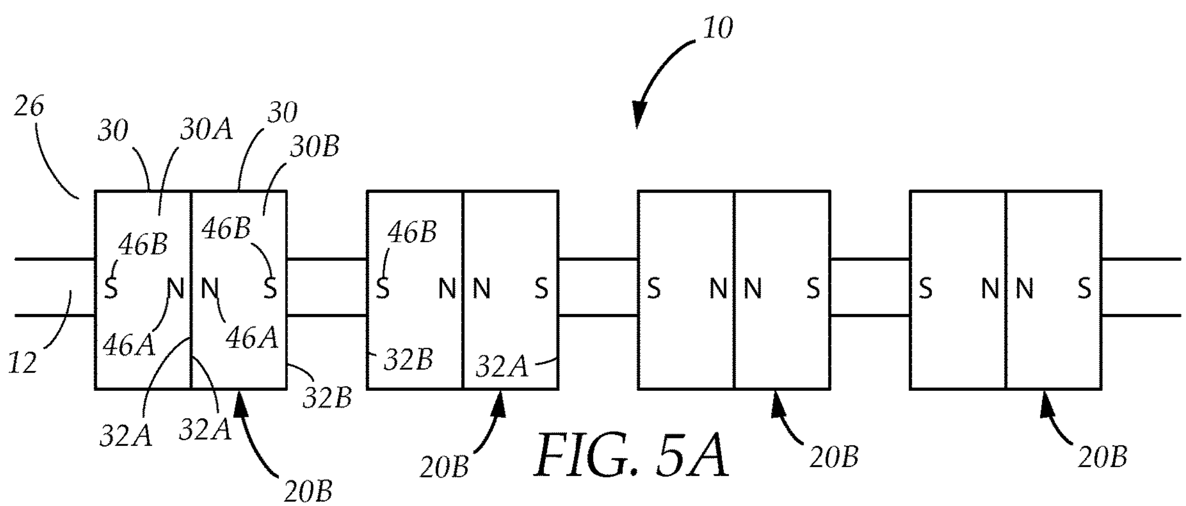
FIG. 5A is a diagrammatical side view of a sequence of alternate magnetic components, in accordance with an embodiment in the present disclosure.
Figure 5B:
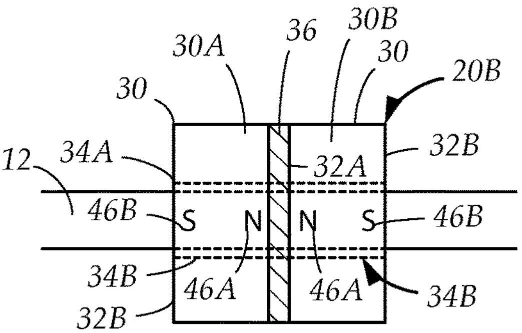
FIG. 5B is a side sectional view of two repelling magnetic subcomponents held in contact by an adhesive bonding means, in accordance with an embodiment in the present disclosure.
Figure 5C:
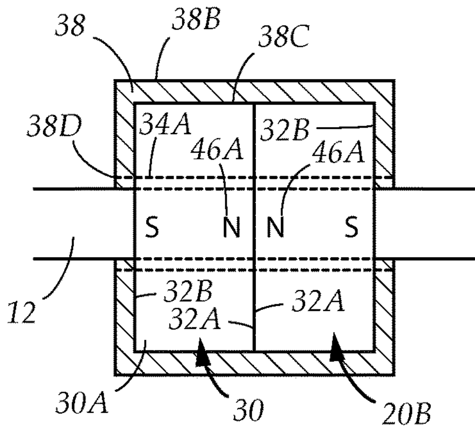
FIG. 5C is a side sectional view of two magnetic subcomponents held in contact in the repelling configuration within a containing shell, in accordance with an embodiment in the present disclosure.

Referring to FIG. 4C while also referring to FIG. 1B, FIG. 3B, and FIG. 4A, an exemplary repelling magnet assembly 10 is shown arranged in a loop configuration 19. The retaining member 12 is formed as a circular or ring-like structure which allows the repelling sequence 26 to annularly surround a portion of the wearer's body such as the wrist 66. When in the loop configuration 19, the repelling magnet assembly 10 has a loop interior space 19B through which the wrist 66 or other portion of the body, such as a leg or neck, may extend. The repelling configuration causes the magnetic fields 40 of the magnetic components 20 within the repelling sequence 26 to be directed inwardly in relation to the loop 19 towards the loop interior space 19B, and towards the body of the wearer 60. In one embodiment, the retaining member 12 is formed of a material with sufficient strength to prevent deformation as a result of the repelling forces 44 exerted by the magnetic components 20. For example, the retaining member 12 may be formed of a rigid plastic material or non-ferrous metal which prevents deformation off the loop configuration 19.

Turning to FIG. 3B and FIG. 4B while also referring to FIG. 4C, the repelling force 44 exerted between the adjoining magnetic components 20 may be strengthened by increasing the number of the magnetic components 20 in relation to the length of the retaining member 12. The repelling force 44 is inversely proportional to the length of the separation interval 28. For example, by maintaining the same length of the retaining member 12 but doubling the number of magnetic components 20 within the repelling sequence 26, the separation interval 28 between each of the adjoining magnetic components 20 will be reduced. Furthermore, increasing the number of magnetic components 20 further concentrates additional magnetic fields 40 within the loop interior space 19B. In one example, the separating interval 28 between each pair of adjacent magnetic components 20 may be less than a corresponding thickness of each magnetic component 20 as measured between the component first face 22A and the component second face 22B. The separating intervals 28 may be minimized by maximizing the number of the magnetic components 20, and/or by altering the magnetic strength of each of the magnetic components 20 through the ferromagnetic composition.

In certain embodiments where the retaining member 12 forms a loop configuration 19, the magnetic components 20 within the repelling sequence 26 form a continuous circular sequence whereby each of the magnetic components 20 repels the magnetic components 20 adjacent to it. The number of magnetic components 20 can be maximized by increasing the number of magnetic components 20 until the length of the retaining member 20 can accommodate no further magnetic components 20, and/or until the repelling forces 44 are so great that no further magnetic components 20 may be added.

Turning now to FIG. 2B and FIGS. 5A-C while also referring to FIG. 2A. FIG. 3B, and FIG. 4A, in an alternate embodiment, the repelling sequence 26 can be formed using a plurality of alternate magnetic components 20B each comprising two magnetic subcomponents 30, corresponding to a first magnetic subcomponent 30A and a second magnetic subcomponent 30B. Note that each alternate magnetic component 20B may be arranged to form repelling sequences 26 in substantially the same manner as magnetic components 20, in accordance with the principles of the present disclosure.

In one embodiment, each magnetic subcomponent 30 has a subcomponent first face 32A, a distally oriented subcomponent second face 32B, and a subcomponent body 30C which extends therebetween. As with the magnetic components 20, each magnetic subcomponent 30 contains ferromagnetic metals and can be configured in a variety of shapes. For example, each magnetic subcomponent 30 can be formed as a disc, with a cylindrical subcomponent outer surface 32C which extends between the subcomponent first face 32A and the subcomponent second face 32B. Each magnetic subcomponent 30 further has a subcomponent channel opening 34A positioned on each of the subcomponent first and second faces 32A, 32B and a subcomponent channel 34B extending therebetween.

In a preferred embodiment, each magnetic subcomponent 30 has a first magnetic pole 46A oriented with the subcomponent first face 32A and a second magnetic pole 46B oriented with the component second face 32B. Each alternate magnetic component 20B is formed by joining the subcomponent first face 32A of the first magnetic subcomponent 30A to the subcomponent first face 32A of the second magnetic subcomponent 30B. The repelling force 44 exerted between the first and second magnetic subcomponents 30A, 30B can be overcome by using a strong bonding means 36 which maintains the physical contact between the first and second magnetic subcomponents 30A, 30B. The bonding means 36 may be a strong adhesive. Alternatively, the subcomponent first faces 32A of the first and second magnetic subcomponents 30A, 30B may be configured with complementary attachment threads creating a threaded bond therebetween.

In another embodiment, the first and second magnetic subcomponents 30A, 30B are held within a containing shell 38. The containing shell 38 is substantially hollow and has a shell outer surface 38B with a shell cavity 38C formed within. The shell cavity 38C is configured to substantially match the shape and dimensions of the alternate magnetic component 20B, and is sufficiently strong to hold the first and second magnetic subcomponents 30A, 30B in direct contact and prevent the separation thereof. In one example, the alternate magnetic component 20B is formed as a cylinder, and the shell cavity 38C is suitably formed in a cylindrical configuration. The containing shell 38 may be formed using materials such as hard plastic which have sufficient strength to overcome the repelling force 44 without interfering with the magnetic fields 40.

The containing shell 38 further has a pair of shell cavity openings 38D, each of which directly align with the subcomponent channel 34B and subcomponent channel openings 34A of the first and second magnetic subcomponents 30A, 30B to allow the retaining member 12 to pass therethrough.

In a preferred embodiment, the subcomponent second faces 32B and the second magnetic poles 46B of the first and second subcomponents 30A, 30B face outwardly away from the abutting subcomponent first faces 32A. As a result, each alternate magnetic subcomponent 20B will always repel any alternate magnetic subcomponent 20B which is adjacent thereto within the repelling sequence 26.

Each magnetic subcomponent 30 within the alternate magnetic component 20B emits a magnetic field 40, which is then repelled by both the repelling force 44 exerted between the first magnetic poles 46A of the first subcomponent 30A and the second subcomponent 30B, and by the repelling force 44 exerted by the second magnetic pole 46B of each alternate magnetic component 20B adjacent thereto. Furthermore, as the distance between the first magnetic poles 46A of the first and second magnetic subcomponents 30A, 30B is minimal, the strength of the repelling force 44 exerted therebetween is greatly increased, causing an increased widening of the magnetic fields 40 emitted by the alternate magnetic components 20B.

Turning to FIG. 4B, in one embodiment, placing two like magnetic polarities in close proximity through the repelling configuration of the repelling sequence 26, creates a magnetic collision which increases movement of free electrons 42 within the magnetic field 40, and has the potential to alter voltage within cells of the human body, as well as increase pH levels in water.

Turning now to FIGS. 6A-B while also referring to FIG. 3B and FIG. 4C, the retaining member 12 can be placed in a segment configuration 19S which can be substantially linear or arcuate in form. The retaining member 12 in the segment configuration 19S may have a first end 12A and a second end 12B, and the magnetic components 20 may be threaded over the retaining member 12 to be held between the first and second ends 12A, 12B. The first and last magnetic components within the repelling sequence 26 may abut against a retaining end 16 disposed at the first and second ends 12A, 12B of the retaining member 12. The retaining ends 16 have a width greater than the width of the channel opening 24A or channel 34, and thus prevent the repelling forces 44 from increasing the separation intervals 28 between the magnetic components 20 and widening the repelling sequence 26. Alternatively, in certain embodiments, the outermost magnetic components 20 within the repelling sequence 26 may be bonded or adhered to the retaining member 12.

In one embodiment, the loop configuration 19 may allow the retaining member 12 to be selectively opened or closed to facilitate ease of wear and removal. As such, the retaining member 12 is fashioned into circular or ring-like shape, and the first end 12A and the second end 12B are detachable, and are joined together by a fastening means 18 positioned therebetween. In one embodiment, the fastening means 18 may correspond to clasp mechanisms 18C, such as jewelry clasps, which are positioned on the first and second ends 12A, 12B. Note that other fastening means 18 and fasteners may be used, as will be appreciated by a person of ordinary skill in the art in the field of the invention. For example, the fastening means 18 may encompass a variety of detachable fasteners suitable for use with jewelry and other wearable accessories.

In certain embodiments, the repelling magnet assembly 10 may be worn as an attachment to a chain, string, or other suitable hanging means connected to the first and second ends 12A, 12B of the retaining member 12. In other embodiments, the repelling magnet assembly 10 may be held close to the body through integration into articles of clothing.

Turning to FIGS. 7A-C while also referring to FIGS. 3A-B, the magnetic components 20 may be formed into various shapes such as elongated cylinders or as rectangular prisms, without altering the arrangement of magnetic poles as described herein. Furthermore, in certain embodiments, the retaining member 12 and the channel opening 24A and/or channel 24B may be configured with alternative cross sectional shapes. For example, the channel opening 24A, the channel 24B, and the retaining member 12 may have a round cross sectional shape, or a square or polygonal cross sectional shape.

Figures 8A, 8B:
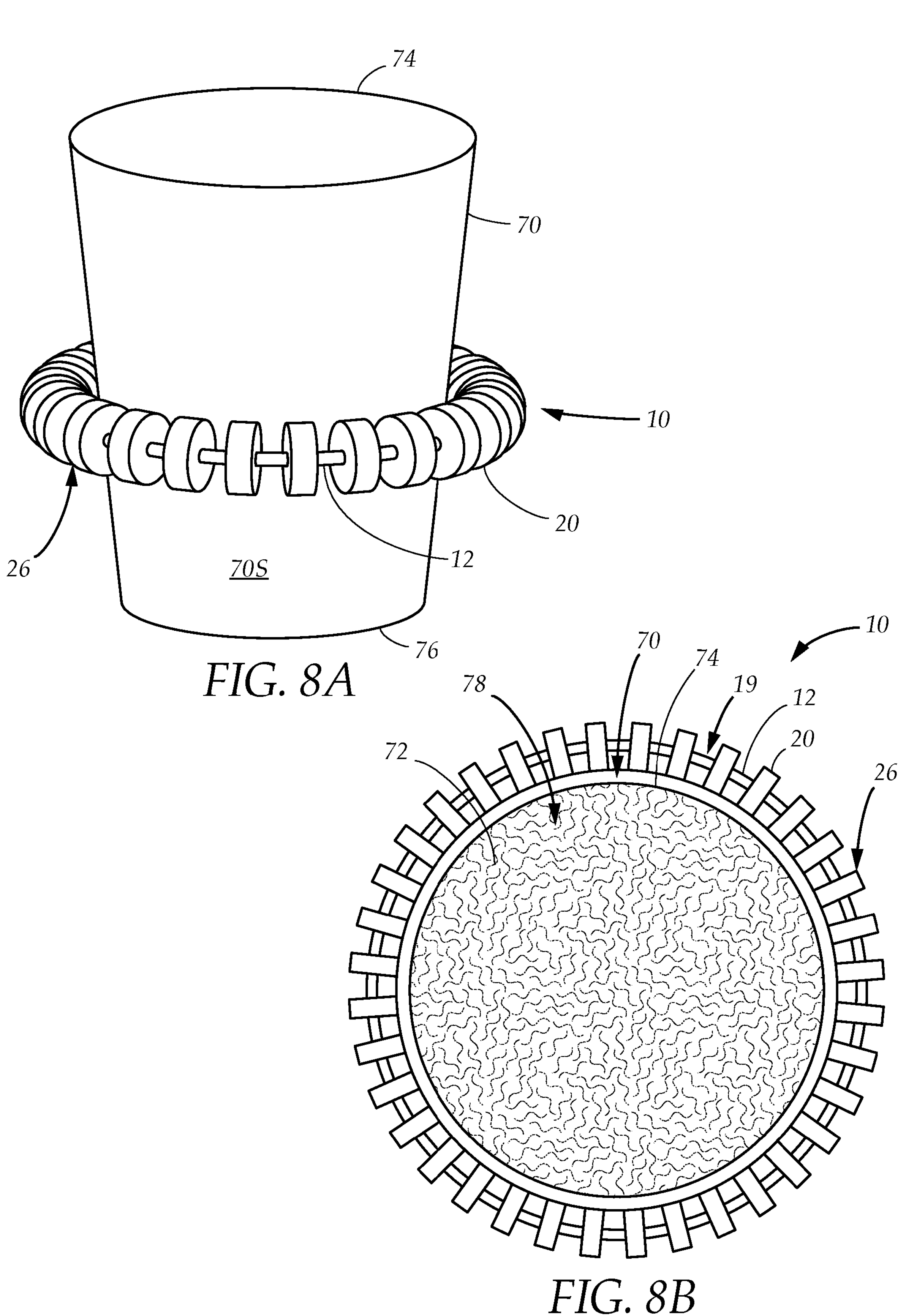
FIG. 8A is a diagrammatical perspective view of the repelling magnet assembly employed with a liquid container, in accordance with an embodiment in the present disclosure.
FIG. 8B is a diagrammatical top view of the repelling magnet assembly surrounding the liquid container, further showing the container interior holding a liquid, in accordance with an embodiment in the present disclosure.

Turning now to FIGS. 8A-B while also referring to FIG. 4C, in an alternative embodiment, the repelling magnet assembly 10 in the loop configuration 19 may be arranged to surround a container 70 for storing a liquid 78, such as a cup or bottle. The container 70 may have a container opening 74, a container base 76, and a container surface 70S extending therebetween. The container 70 further has a container interior 72 for holding the liquid 78, which is accessible via the container opening 74. The repelling magnet assembly 10 may be positioned between the container opening 74 and the container base 76 to surround the container surface 70S. The magnetic fields 40 emitted by the repelling sequence 26 extend inwardly into the interior space 19S to pass through the liquid 78, thus allowing the magnetic fields 40 to increase the pH level of the liquid 78.

Figure 9:
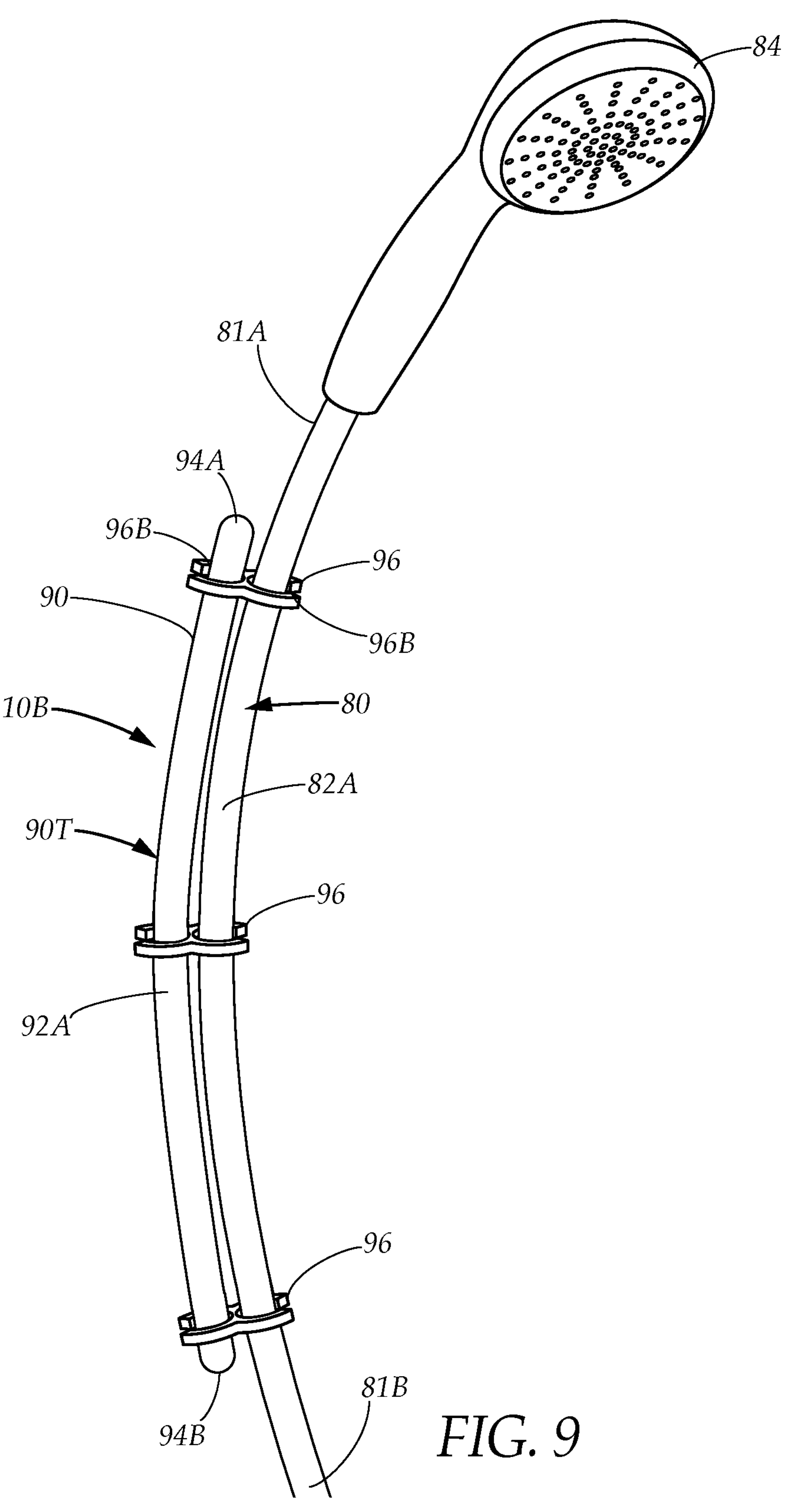
FIG. 9 is a diagrammatical view of a detachable repelling magnetic assembly secured to a flexible water hose, in accordance with an embodiment in the present disclosure.
Figure 10A:
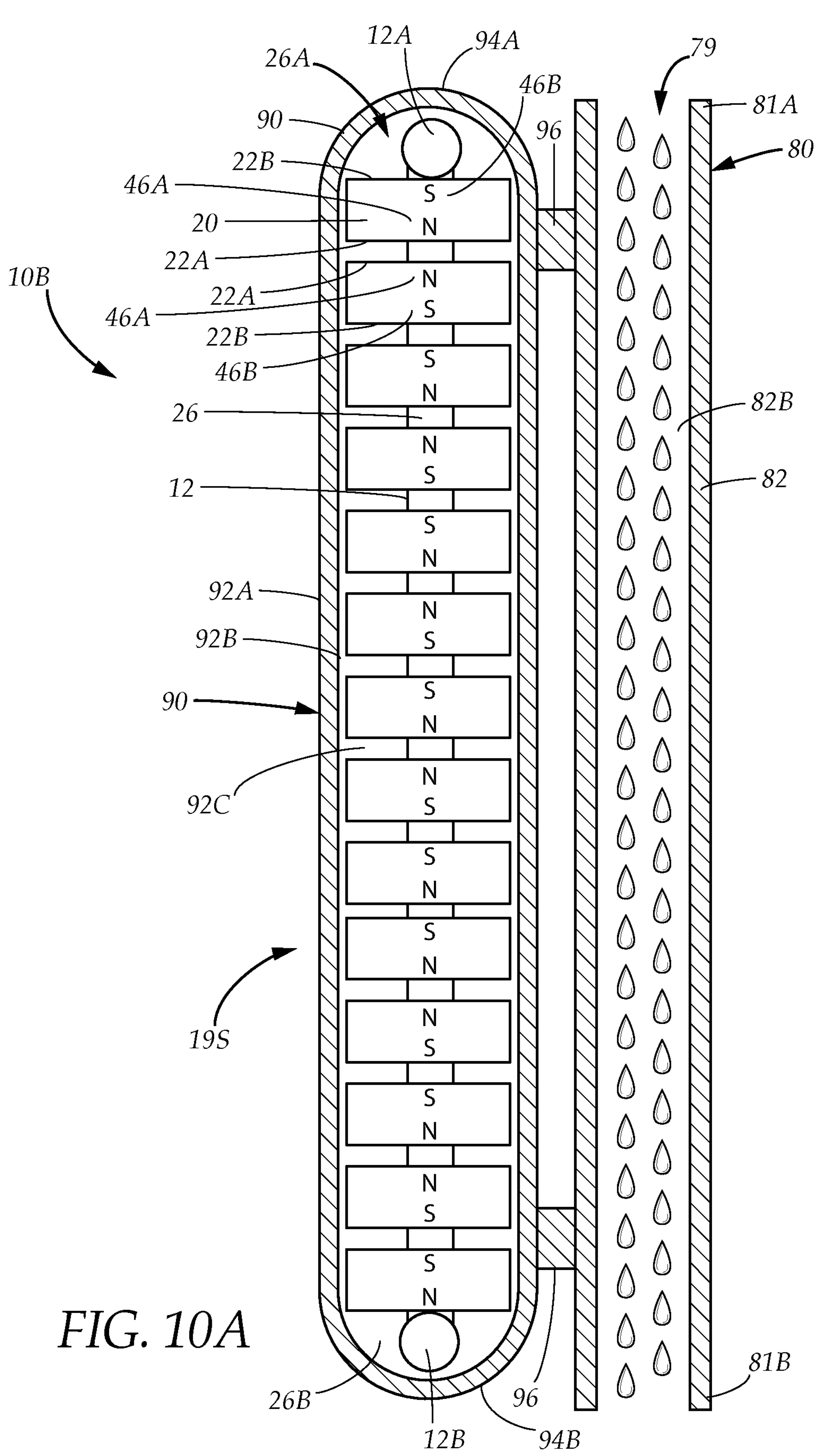
FIG. 10A is a diagrammatical view of a repelling sequence of magnetic components enclosed within an outer casing, in accordance with an embodiment in the present disclosure.
Figure 10B:
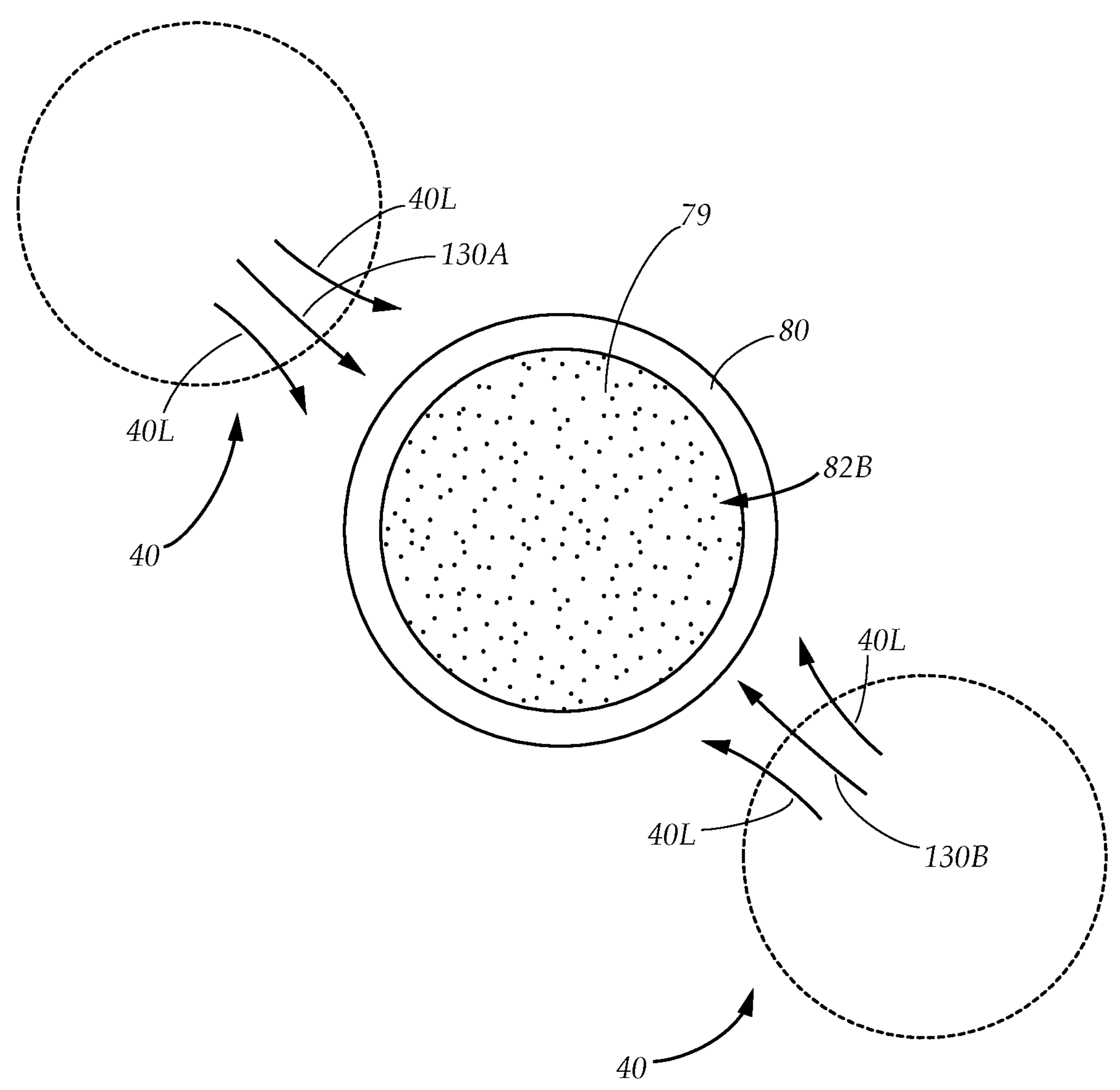
FIG. 10B is a diagrammatical cross sectional view depicting the water pipe, further depicting magnetic field lines being directed towards the water within the pipe, in accordance with an embodiment in the present disclosure.
Figure 11A:
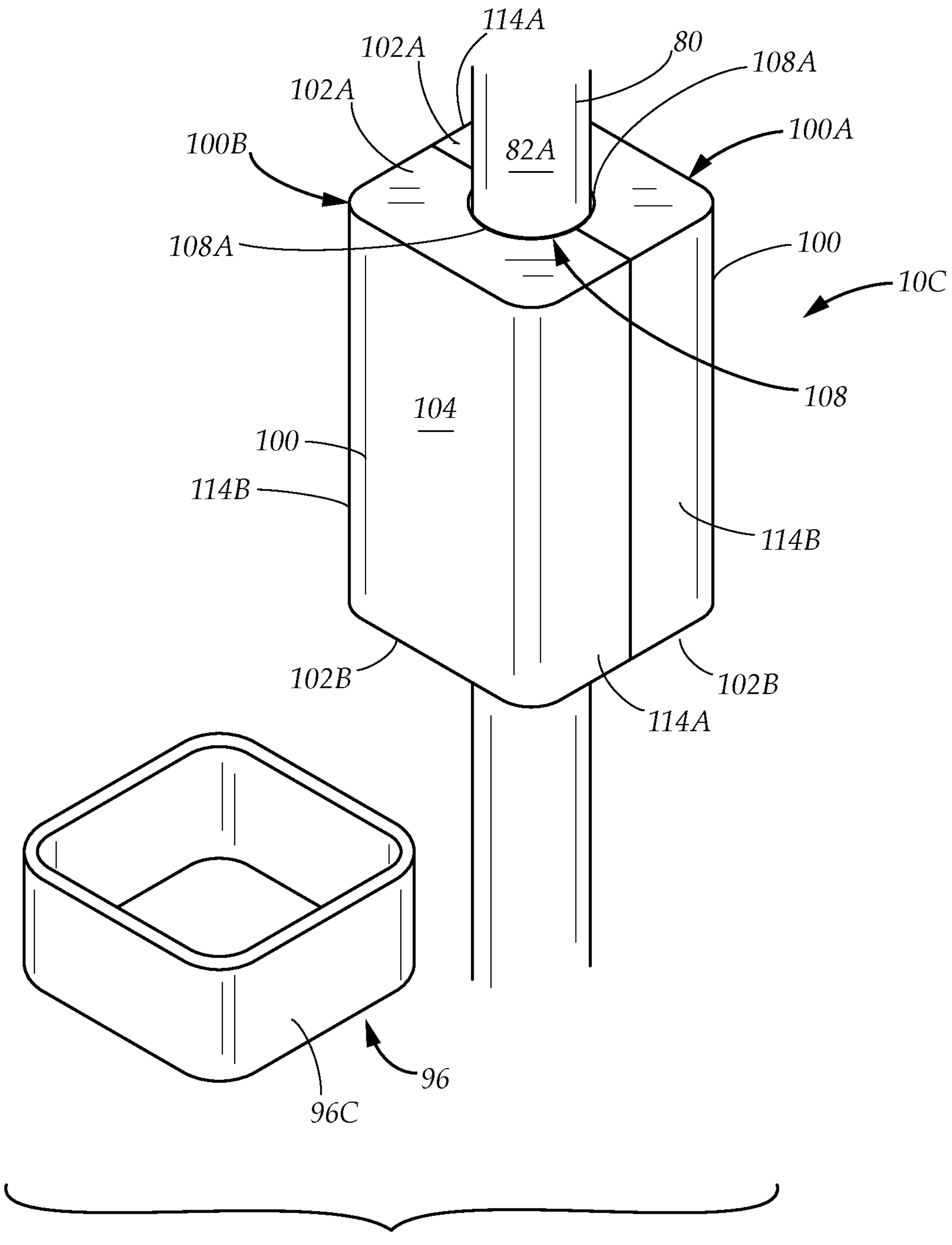
FIG. 11A is a diagrammatical perspective view of a repelling magnet housing attached to a water pipe, further depicting two portions of the housing which contain repelling magnets, and an exemplary fastener adapted to counter the repelling force generated between the portions of the housing, in which the exemplary fastener is configured as a band, in accordance with an embodiment in the present disclosure.
Figure 11B:
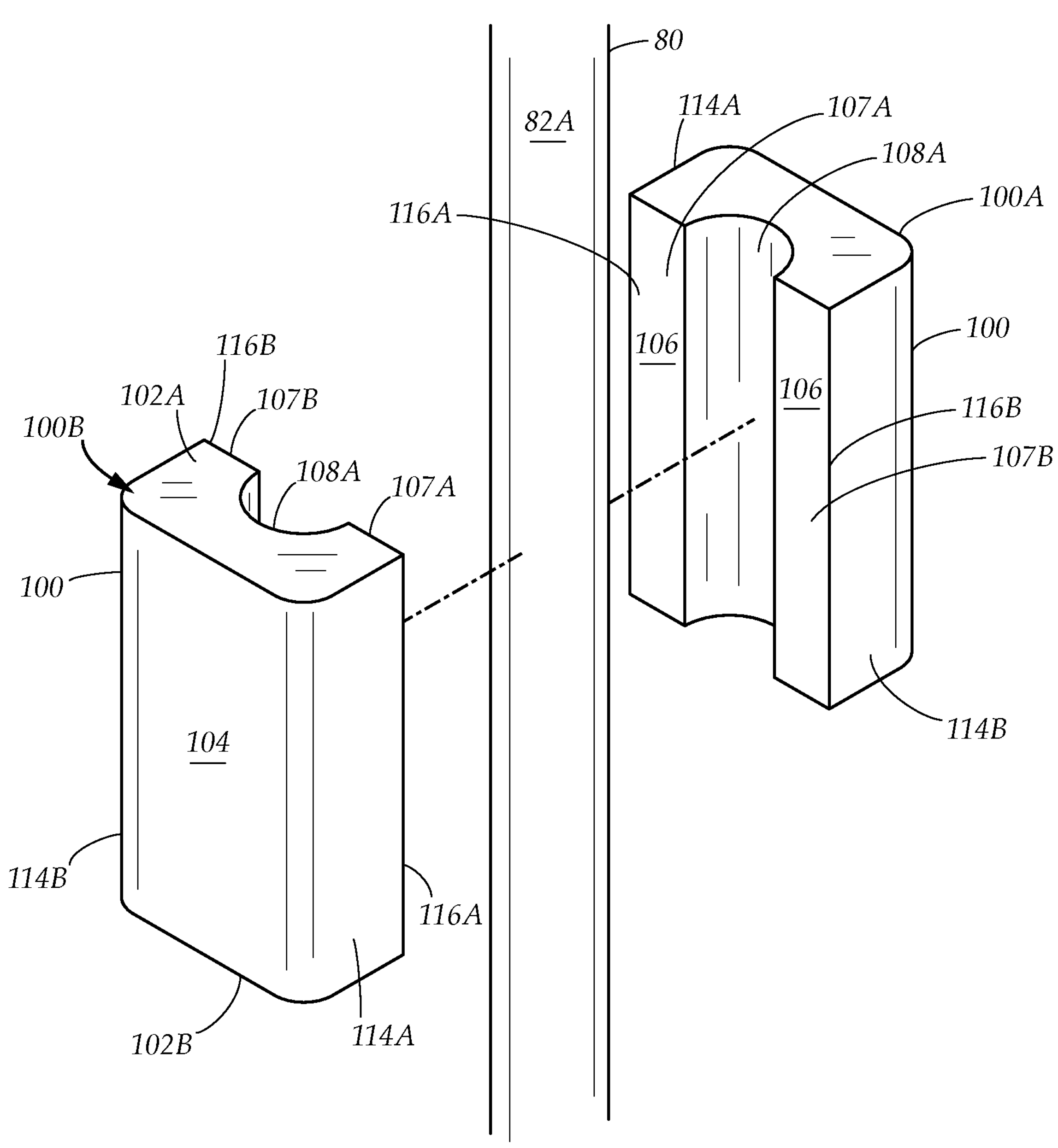
FIG. 11B is a diagrammatical exploded view of the repelling magnet housing divided between the first portion and a second portion but with the fastener omitted, the first portion and the second portion each have a channel recess which combine to form a longitudinal retaining channel, in accordance with an embodiment in the present disclosure.
Figure 11C:
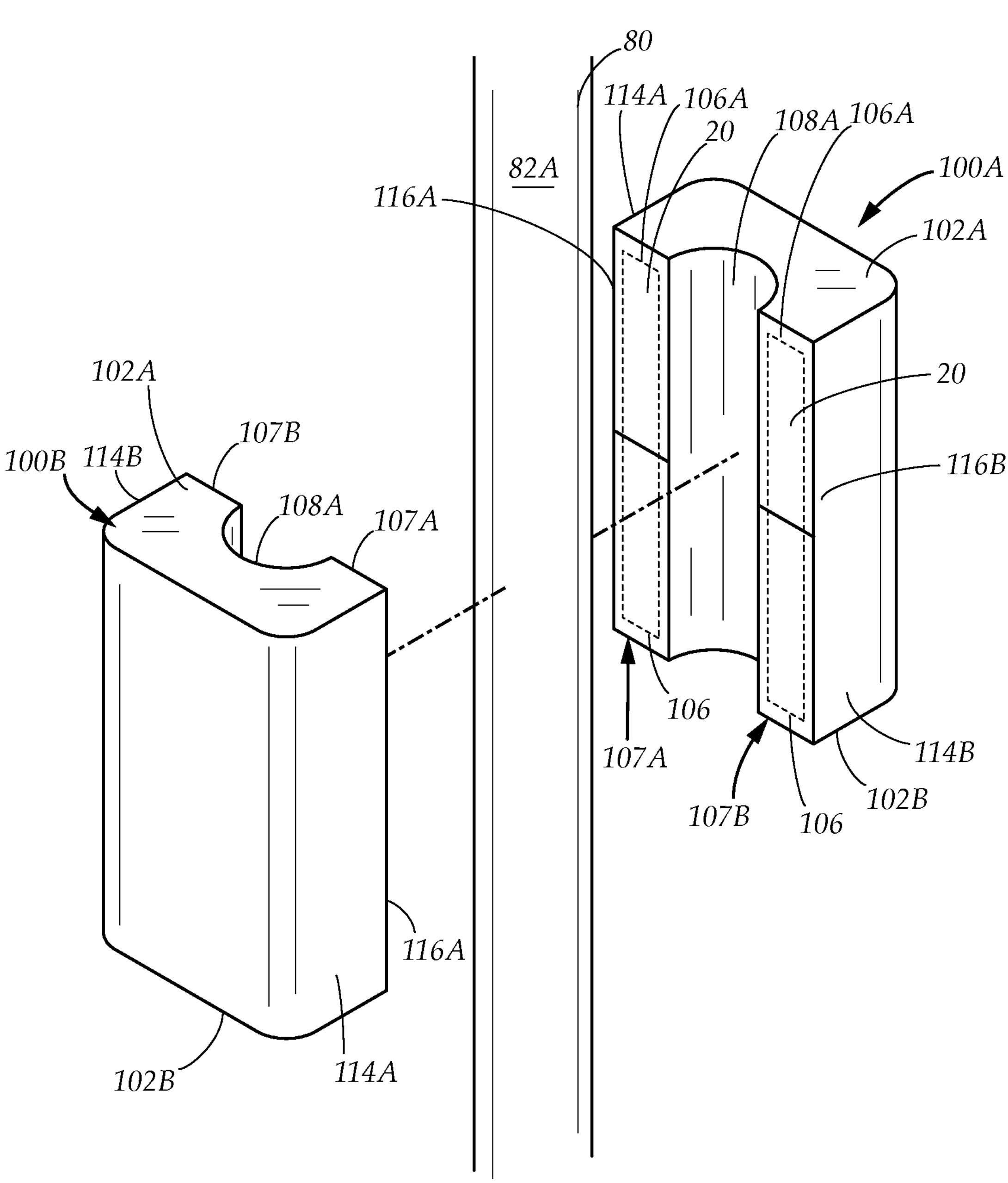
FIG. 11C is a diagrammatical exploded view showing an embodiment of the housing with inner face openings which expose the first face of the magnetic component, in accordance with an embodiment in the present disclosure.
Figure 11D:
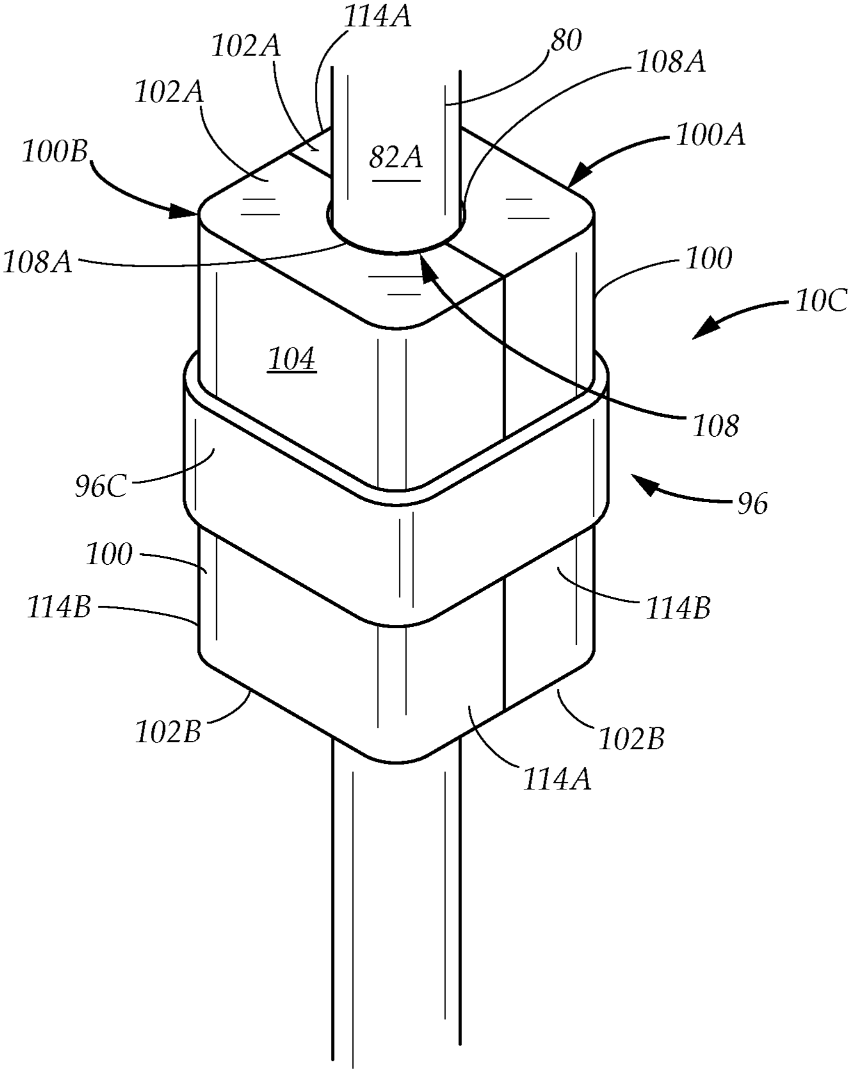
FIG. 11D is a diagrammatical perspective view showing the first portion and the second portion of the housing secured around the water pipe with the fastener in position, in accordance with an embodiment in the present disclosure.

Turning now to FIG. 9 and FIGS. 10A-B, in one embodiment, a repelling sequence 26 of magnetic components 20 arranged in a segment configuration 19S which can be used to for use with a water pipe 80. The water pipe 80 can be a pipe, hose, line, conduit, or other substantially tube-shaped apparatus configured to convey water 79 or another liquid, between a pipe second end 81B and a pipe first end 81A. The water pipe 80 has a pipe exterior 82 and a pipe interior space 82B through which the water 79 can be transported. The pipe exterior 82 can be either rigid or flexible. In one example, the pipe first end 81A may terminate in a showerhead or faucet functioning as a water outflow point through which the water 79 exits the water pipe 80. In certain embodiments, the detachable repelling magnet assembly 10B is adapted for use with a flexible water pipe 80, such as a shower hose capable of flexing motion.

In a preferred embodiment, the detachable repelling magnet assembly 10B comprises an outer casing 90, a retaining member 12, and a plurality of magnetic components 20 formed into a repelling sequence 26 with the magnetic components 20 threaded around the retaining member 12. The retaining member 12 is disposed in a segment configuration 19S, and the repelling sequence 26 has a repelling sequence first end 26A oriented towards the retaining member first end 12A, and a repelling sequence second end 26B oriented towards the retaining member second end 12B. The detachable repelling magnet assembly 10B also comprises a plurality of fasteners 96, which are adapted to allow the detachable repelling magnet assembly 10B to be attached to the water pipe 80.

The outer casing 90 is configured to hold the repelling sequence 26, and comprises a casing first end 94A, a casing second end 94B distally oriented in relation to the casing first end 94A, and a substantially tube-shaped body portion 90T which extends between the casing first end 94A and the casing second end 94B. The body portion 90T has a casing outer surface 92A, and a casing interior space 92B which is adapted to enclose the repelling sequence 26.

The repelling sequence 26 is positioned within the casing interior space 82B with the repelling sequence first end 26A oriented towards the casing first end 94A and the repelling sequence second end 26B oriented towards the casing second end 94B. In a preferred embodiment, the body portion 90T has a diameter which is substantially the same as or slightly greater than the diameter or width of the magnetic components 20. The outer casing 90 has a length, as measured between the casing first end 94A and the casing second end 94B, which is substantially equal to or slightly longer than the length of the repelling sequence 26 between the repelling sequence first end 26A and the repelling sequence second end 26B.

In a preferred embodiment, the outer casing 90 is adapted to prevent the magnetic components 20 from being exposed to water, and the repelling sequence 26 may be fully sealed within the casing interior space 92C. This allows the magnetic components 20 to be fully protected from water when used in an environment such as a bath or shower. The body portion 90T may be formed of a flexible, impermeable material such as PVC, polyurethane, silicone, polyethylene, rubber, or other suitable material as will be appreciated by a person of ordinary skill in the art in the field of the invention.

Furthermore, in a preferred embodiment, the retaining member 12 is formed of a flexible material, such as metal, plastic, thermoplastic, or other suitable material, which allows the repelling sequence 26 to flex and bend along its length between the retaining member first end 12A and the remaining member second end 12B.

The fasteners 96 are adapted to secure the outer casing 90 to the pipe exterior 82 in a linear alignment position, in which the outer casing 90 and the repelling sequence 26 are parallel to the water pipe 80, the casing first end 94A and the repelling sequence first end 26A are oriented towards the pipe first end 81A, and the casing second end 94B and the repelling end second end 26B are oriented towards the pipe second end 81B. In an embodiment, the fasteners 96 are attached to the casing outer surface 92A, and each fastener 96 has a clip portion 96B which projects laterally to grip the pipe exterior 82. The clip portion 96B may comprise a pair of arms separated by a space, configured to detachably secure the outer casing 90 to the water pipe 80. Note that the fasteners may be implemented using alternate means configured to detachably secure the outer casing 90 to the water pipe 80, such as releasable hook and loop tape, bands, belts, clasps, rings, or other appropriate means.

The plurality of fasteners 96 are disposed along the outer casing 90 between the casing first end 92A and the casing second end 92B, allowing the outer casing 90 to match the flexing motion of the portion of the water pipe exterior 82 to which the outer casing 90 is attached via the fastener 96, thus allowing the outer casing 90 and the repelling sequence 26 to remain in linear alignment with the water pipe 80 as it undergoes flexing movement. For example, at least three fasteners 96 may be employed, with one fastener positioned proximate to the casing first end 94A, a second fastener positioned proximate to the casing second end 94B, and at least one fastener positioned therebetween.

The magnetic components 20 of the repelling sequence 26 are positioned adjacent to the water pipe 80, allowing the magnetic fields 40 to pass through the pipe exterior 82 to the pipe interior space 82B and the water 79 contained therein. To increase the exposure of the water 79 to the magnetic fields 40 of the repelling sequence, the length of the outer casing 90 and the repelling sequence 26 can extend up to the length of the water pipe 80 as measured between the pipe first end 81A and the pipe second end 81B, thus allowing the water 79 to be continuously exposed to the magnetic fields 40 until the water 79 exits the water pipe 80.

Note however, that in certain alternate embodiments, the water pipe 80 may not be flexible, and the outer casing 90 and the retaining member 12 may be formed of materials which are rigid or otherwise do not impart flexibility to the detachable repelling magnet assembly 10B.

In certain embodiments, two or more detachable repelling magnet assemblies 10B can be attached to one water pipe 80. For example, one of the detachable repelling magnet assemblies 10B can be positioned in linear alignment with the water pipe 80 at a first source direction 130A, while another of the detachable magnet assemblies 10B can be positioned in linear alignment with the water pipe 80 at a second source direction 130B. As indicated by the magnetic field lines 40L, the magnetic fields 40 can be projected through the water pipe 80 from both the first source direction 130A and the second source direction 130B.

Turning now to FIGS. 11A-C and 12A while also referring to FIG. 4A, a detachable repelling magnet housing 10C is shown. The detachable repelling magnet housing 10C comprises a first portion 100A and a second portion 100B, and the first portion 100A and the second portion 100B each contain a magnetic component 20. The first portion 100A and the second portion 100B are further adapted to fit together in an abutting position to surround and enclose a portion of the water pipe 80, causing the magnetic components 20 of the first portion 100A and the second portion 100B to exert a repelling force therebetween, while also exposing the water 79 within the water pipe 80 to the magnetic fields 40.

In a preferred embodiment, the first portion 100A and the second portion 100B each have a shell 100 with a housing first end 102A, a housing second end 102B distally oriented in relation to the housing first end 102A, a housing inner face 106 extending between the housing first end 102A and the housing second end 102B, and one or more housing interior spaces 112 each configured to hold one of the magnetic components 20. In a preferred embodiment, the first portion 100A and the second portion 100B are substantially identical.

The housing inner face 106 of both the first portion 100A and the second portion 100B each have a channel recess 108A which extends longitudinally between the housing first end 102A and the housing second end 102B. In a preferred embodiment, the water pipe exterior 82 is cylindrical, and the channel recesses 108A are semi-cylindrical in shape. The first portion 100A and the second portion 100B are adapted to be placed in an abutting position, in which the channel recesses 108A of the first portion 100A and the second portion 100B are aligned while the housing inner faces 106 abut against each other. The channel recesses 108A combine to form a longitudinal retaining channel 108. In one embodiment, the housing first ends 102A of the first portion 100A and the second portion 100B are both disposed towards the pipe first end 81A, while the respective housing second ends 102B are disposed towards the pipe second end 81B.

The longitudinal retaining channel 108 is adapted to circumferentially grip the pipe exterior 82 and secure the detachable repelling magnet housing 10C to the water pipe 80. As such, the longitudinal retaining channel 108 may have a circular cross section with a diameter which is configured to substantially match the diameter of the water pipe 80. The detachable repelling magnet housing 10C and the longitudinal retaining channel 108 may be sized to fit various standardized water pipe diameters. In certain embodiments, the channel recesses 108A may be coated with a compressible friction layer to grip the pipe exterior 82. The compressible friction layer may be formed of rubber, silicone, or other suitable material.

Figure 12A:
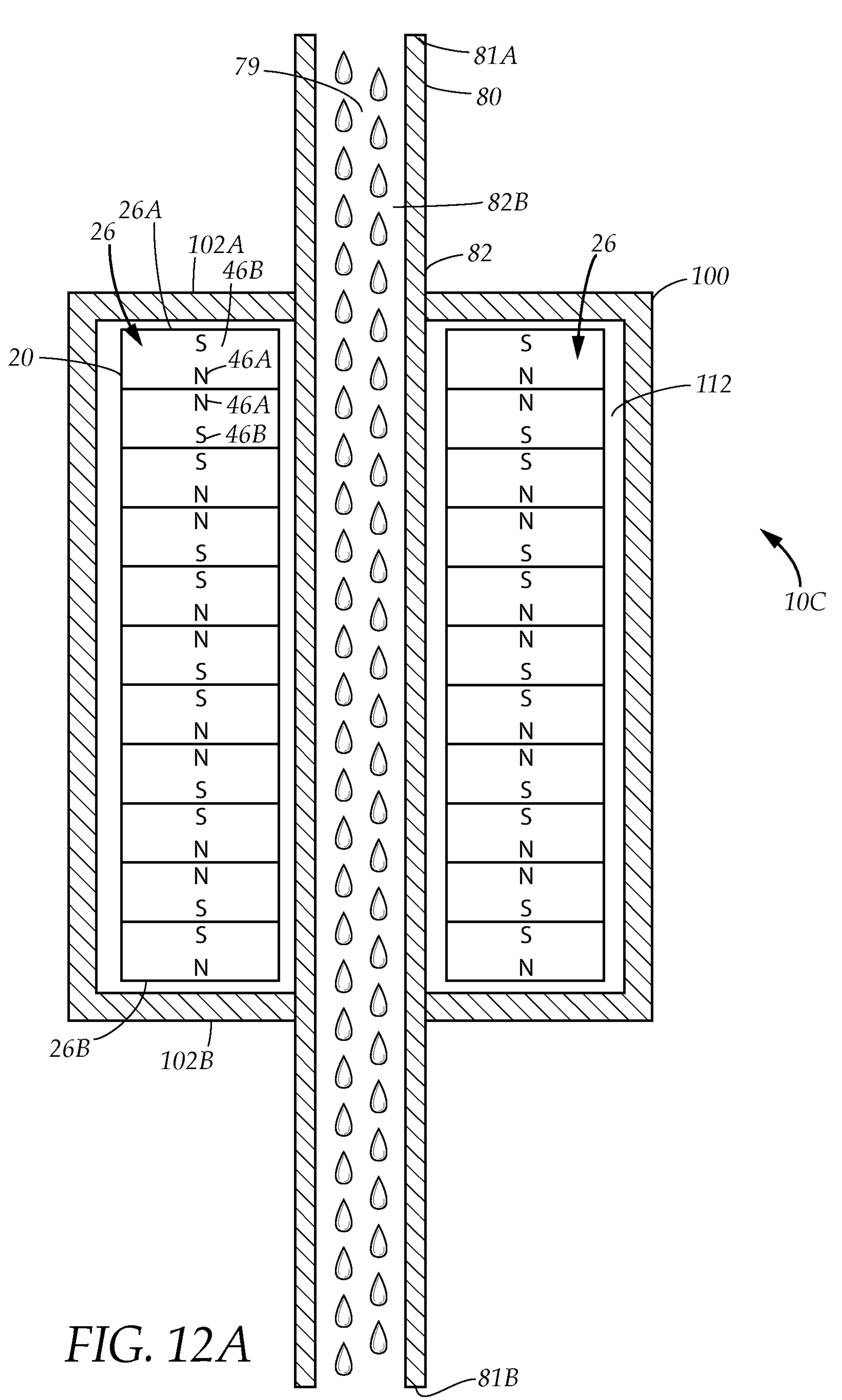
FIG. 12A is a diagrammatical side sectional view showing a housing interior space holding two repelling sequences of magnetic components, in accordance with an embodiment in the present disclosure.
Figure 12B:
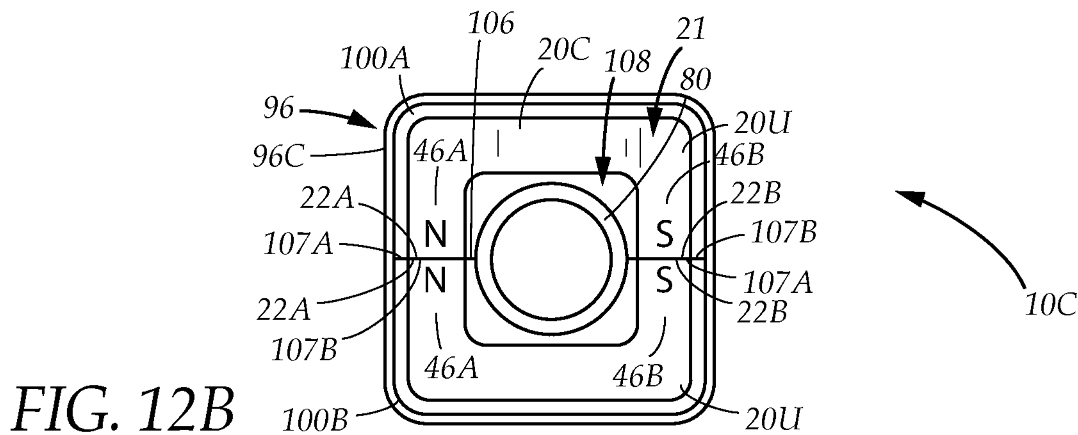
FIG. 12B is a diagrammatical top sectional view of the repelling magnet housing, showing a horseshoe magnet positioned within the first portion and the second portion of the housing with the magnet faces coplanar with the housing inner face, further depicting the fastener positioned to prevent the repelling force from separating the portions of the housing in accordance with an embodiment in the present disclosure.

Turning to FIG. 12B while continuing to refer to FIGS. 11A-C and FIG. 12A, in one embodiment, the channel recesses 108 bisect the housing inner face 106 of the first portion 100A and the second portion 100B to form two contact surfaces comprising a first contact surface 107A and a second contact surface 107B.

The magnetic component 20 may be formed as a horseshoe magnet 20U with a magnet first face 22A and a magnet second face 22B each exhibiting a first magnetic pole 46A and a second magnetic pole 46B respectively. The horseshoe magnet 20U further has a component body 20C extending between the magnet first face 22A and the magnet second face 22B. The component body 20C forms a connecting curve 21, which places the magnet first face and the magnet second face in coplanar alignment.

When the horseshoe magnet 20U is positioned within the housing interior space 112 of the first portion 100A or the second portion 100B, the connecting curve 21 aligns longitudinally with the channel recess 108A, and the magnet first face 22A and the magnet second face 22B are each aligned with either the first contact face 107A or the second contact face 107B of the housing inner face 106. For example, the magnet first face 22A may be disposed at the first contact face 107A while the magnet second face 22B may be disposed at the second contact face 107B. In some embodiments, the horseshoe magnet 20U may have a length which is slightly less than the distance between the housing first end 102A and the housing second end 102B. As such, the first portion 100A and the second portion 100B may each contain a single horseshoe magnet 20U configured as the magnetic component 20.

In certain embodiments, the housing inner face 106 has one or more inner face openings 106A positioned at the first contact face 107A and the second contact face 107B. The magnet first face 22A and the magnet second face 22B may therefore pass through the corresponding inner face opening 106A to become coplanar with the housing inner face 106. In other embodiments, the magnet first face 22A or the magnet second face 22B may extend outwardly beyond the housing inner face 106. However, in certain embodiments, the housing inner face 106 lacks the inner face openings 106A, and the magnet first face 22A and the magnet second face 22B may abut against the shell 100 from within the housing interior space 112.

When the first portion 100A and the second portion 100B are placed in the abutting position, the magnetic components 20 of the first portion 100A and the second portion 100B exert a repelling force therebetween. The horseshoe magnets 20U are held within the first portion 100A and the second portion 100B in a mirrored arrangement, such that the magnet first faces 22A and the magnet second faces 22B are positioned in opposition to allow the magnetic first poles 46A and the magnetic second poles 46B to repel each other.

In embodiments where the inner face openings 106A are present, the magnet first faces 22A and the magnetic second faces 22B of the first portion 100A and the second portion 100B are placed in direct contact, thus maximizing the repelling force generated between the matching magnetic first poles 46A and the magnetic second poles 46B.

Furthermore, when placed in the abutting position, the connecting curves 21 of the horseshoe magnets 20U of the first portion 100A and the second portion 100B combine to circumferentially surround the longitudinal retaining channel 108, as well as the water pipe 80 enclosed therein.

Figure 12C:
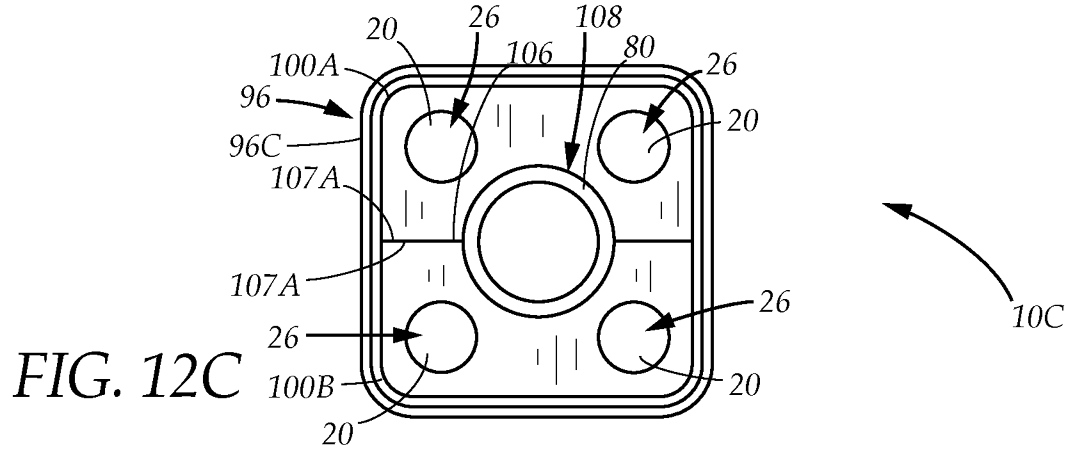
FIG. 12C is a diagrammatical top sectional view of the repelling magnet housing, showing a plurality of repelling sequences arranged in parallel with the water pipe, in accordance with an embodiment in the present disclosure.
Figure 12D:
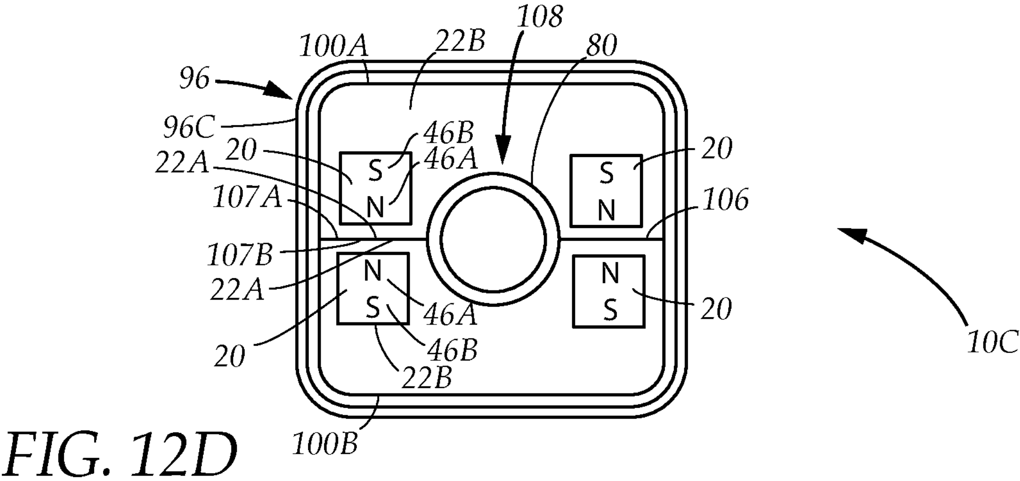
FIG. 12D is a diagrammatical top sectional view of the repelling magnet housing, showing a plurality of magnetic components within the first portion and the second portion, in accordance with an embodiment in the present disclosure.

Turning to FIG. 12D while continuing to refer to FIGS. 11A-C and FIGS. 12A-B, in another embodiment, the first portion 100A and the second portion 100B each contain at least two magnetic components 20 instead of a horseshoe magnet 20U. These magnetic components 20 may be disc shaped, cylindrical, or bar shaped, with the magnet first face 22A oriented directly away from the magnet second face 22B. The two magnetic components 20 are positioned at the first contact face 107A and the second contact face 107B with either the magnet first face 22A or the magnet second face 22B oriented outwardly.

Turning to FIG. 12C while also referring to FIGS. 10A-B, FIGS. 11A-C and FIG. 12A, in another embodiment, the first portion 100A and the second portion 100B may each contain at least one repelling sequence 26 of magnetic components 20 disposed longitudinally in parallel with the longitudinal retaining channel 108.

Figure 14A:
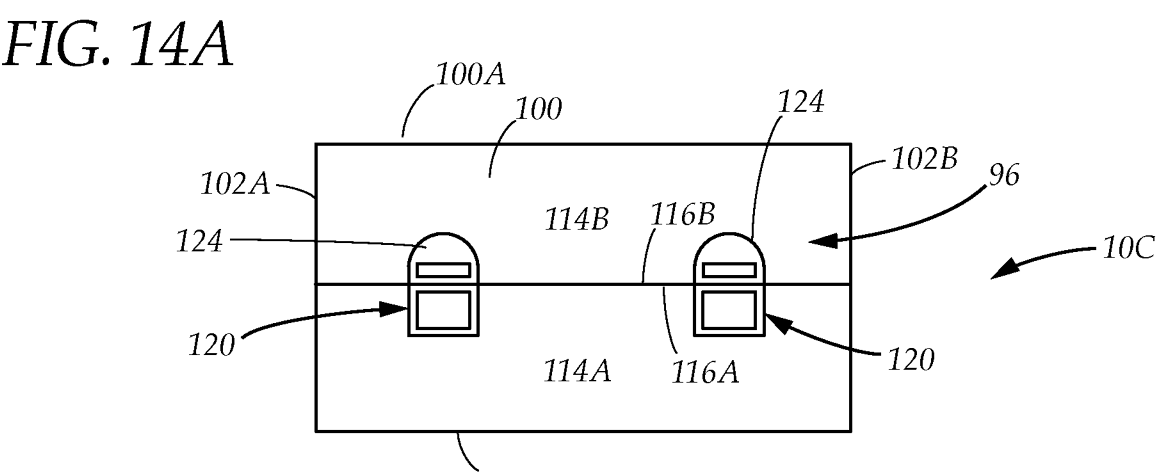
FIG. 14A is a diagrammatical side view of the repelling magnet housing, depicting a plurality of locking latches which function as fasteners to secure the first portion to the second portion, in accordance with an embodiment in the present disclosure.
Figure 14B:
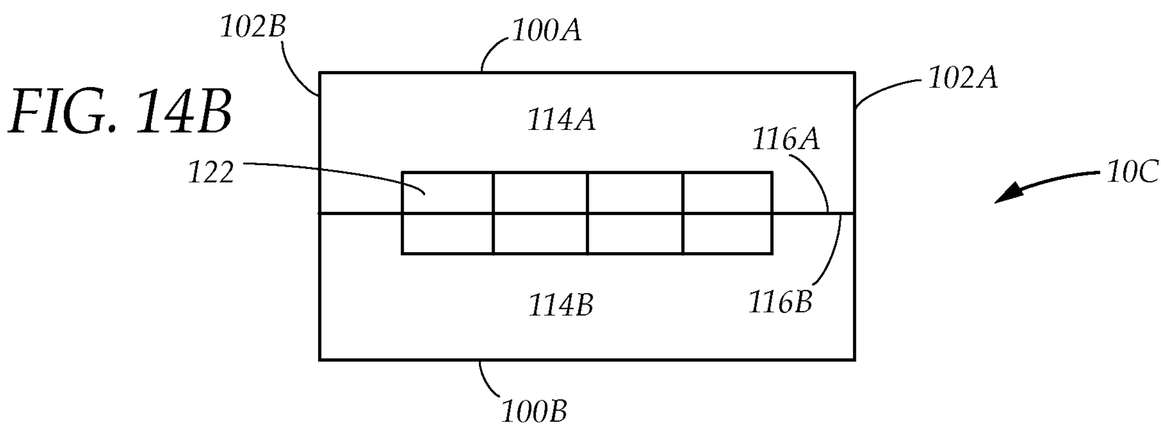
FIG. 14B is a diagrammatical side view of the repelling magnet housing, depicting a hinge assembly which connects the first portion and the second portion, in accordance with an embodiment in the present disclosure.
Figure 14C:
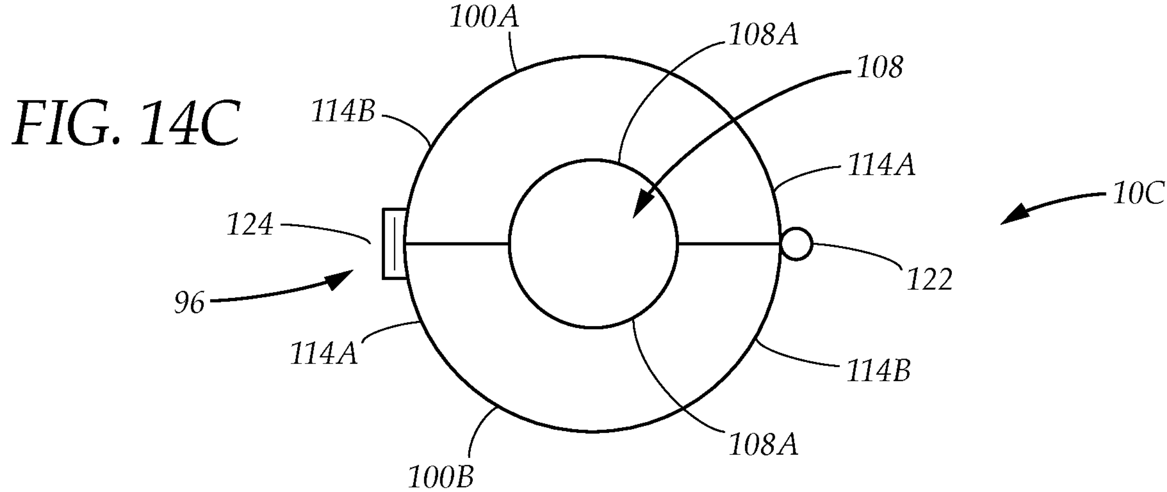
FIG. 14C is a diagrammatical top view of the repelling magnet housing, depicting the locking latch and hinge assembly, in accordance with an embodiment in the present disclosure.

Turning now to FIGS. 14A-C while also referring to FIGS. 11A-D and FIG. 12B, in a preferred embodiment, the detachable repelling magnet housing 10C further comprises a plurality of fasteners 96 adapted to overcome the repelling force and prevent the first portion 100A and the second portion 100B from separating when placed in the abutting position. The fasteners 96 are further configured to allow the first portion 100A and the second portion 100B to be separated when desired, thus allowing the detachable repelling magnet housing 10C to be removed from the water pipe 80.

In one embodiment, the fastener 96 can be implemented as a band 96C adapted to wrap around the first portion 100A and the second portion 100B of the housing 10C, in an orientation transverse to the longitudinal retaining channel 108 and the water pipe 80. In one embodiment, the band 96C can be configured as a belt or loop which wraps around the housing outer face 104, the housing first side 114A, and the housing second side 114B of both the first portion 100A and the second portion 100B. In one embodiment, the band 96C can be formed of various materials which are flexible and strong, thus allowing the band 96C to accommodate the shape of the housing 10C while also overcoming the repelling force. The band 96C can be continuous, or alternatively, can be formed as a strap or belt with two ends which can be separated or joined to form the loop. The two ends can be joined together using a buckle, slide adjuster, or other device which can allow the band 96C to have a variable circumference, as will be apparent to a person of ordinary skill in the pertinent art. In another embodiment, the band 96C may also be formed of a rigid material, and will have a cross sectional shape which matches the cross sectional shape of the housing 10C when viewed from the housing first end 102A or the housing second end 102B. As such, the band 96C in its rigid configuration will be sized to substantially match the shape and dimensions of the housing 10C when the first portion 100A and the second portion 100B are joined in the repelling position, allowing either the housing first end 102A or the housing second end 102B to pass centrally through the band 96C such that the inner surface of the band 96C is flush against the outer surface of the housing 10C. In the rigid configuration, the band 96C can be formed of metal, plastic, or other suitably strong material.

In another embodiment, in lieu of a band 96C, the fasteners 96 correspond to detachable locking mechanisms 120 comprising a releasable latch 124. The first housing 100A and the second housing 100B may each have a housing first side 114A and a housing second side 114B extending parallel to the longitudinal retaining channel 108. The detachable locking mechanisms 120 may be disposed on the housing first sides 114A or the housing second sides 114B to detachably lock the first portion 100A to the second portion 100B. Note that alternative locking mechanisms 120 may be employed, as will be apparent to a person of ordinary skill in the art.

In certain embodiments, the detachable repelling magnet housing 10C may further comprise a hinge assembly 122 which provides a hinged connection between the first portion 100A and the second portion 100B. In one embodiment, the housing first side 114A of the first portion 100A may have a first side edge 116A which is adjacent to a second side edge 116B of the housing second side 114B of the second portion 100B. The hinge assembly 122 may be positioned to hingedly connect the first side edge 116A to the second side edge 116B. The fasteners 96 may be positioned opposite on the housing second side 114B of the first portion 100A and the housing first side 114A of the second portion 100B. The fasteners 96 may be released to allow the first portion 100A and the second portion 100B to pivot about the hinge assembly 122, thus allowing the detachable repelling magnet housing 10C to be removed from around the water pipe 80.

Figure 13:
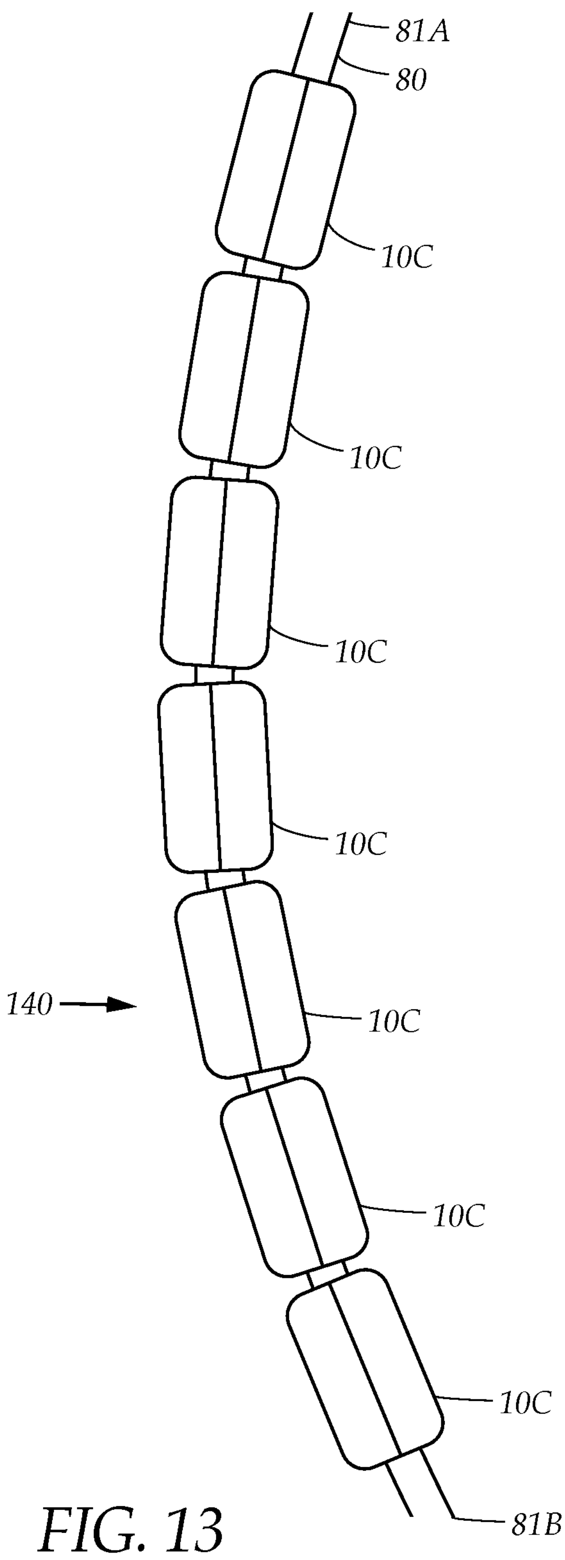
FIG. 13 is a diagrammatical side view of a housing sequence of multiple additional housings attached to the water pipe, in accordance with an embodiment in the present disclosure.

Turning now to FIG. 13 while also referring to FIG. 12A and FIG. 4A, to maximize the exposure of the water 79 within the water pipe 80 to magnetic fields 40 and free electrons, a plurality of detachable repelling magnet housings 10C may be employed. For example, additional detachable repelling magnet housings 10C may be positioned along the water pipe 80 between the pipe first end 81A and the pipe second end 81B, to form a housing sequence 140. Each detachable repelling magnet housing 10C has a length, measured from the housing first end 102A to the housing second end 102B, and the combined lengths of the housing sequence 140 may approach the length of the water pipe 80, while providing sufficient spacing between each of the detachable repelling magnet housings 10C to allow the water pipe 80 to undergo flexing motion.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly. The term "substantially" is defined as at least 95% of the term being described and/or within a tolerance level known in the art and/or within 5% thereof.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a repelling magnet assembly. The disclosure is illustrated by example in the drawing figures, and throughout the written description. It should be understood that numerous variations are possible, while adhering to the inventive concept. Such variations are contemplated as being a part of the present disclosure.

What is claimed is:

1. A repelling magnet assembly for use with a water pipe, the water pipe has a pipe exterior, a pipe first end, a pipe second end, and a pipe interior, the pipe interior is adapted to convey water between the pipe first end and the pipe second end, the repelling magnetic assembly comprising:

a plurality of magnetic components, each magnetic component has a channel and projects a magnetic field;

a retaining member which passes through the channel of each of the magnetic components, the retaining member has a retaining member first end and a retaining member second end;

a repelling sequence formed from the plurality of magnetic components disposed linearly along the retaining member, the repelling sequence has a repelling sequence first end oriented towards the retaining member first end and a repelling sequence second end oriented towards the retaining member second end, each of the magnetic components within the repelling sequence exerts a repelling force against the magnetic components which are adjacent to said magnetic component;

an outer casing, the outer casing has a casing first end, a casing second end, and a casing interior space that extends between the casing first end and the casing second end, the casing interior space is adapted to enclose the repelling sequence, the repelling sequence is disposed within the casing interior space with the repelling sequence first end oriented towards the casing first end and the repelling sequence second end oriented towards the casing second end; and a plurality of fasteners, each of the plurality of fasteners is attached to the outer casing, the fasteners are adapted to secure the outer casing to pipe exterior in a linear alignment position whereby the outer casing is parallel to the water pipe with the casing first end oriented towards the pipe first end and the casing second end oriented towards the pipe second end, such that the water within the water pipe is exposed to the magnetic fields of the magnetic components of the magnetic sequence.

2. The repelling magnet assembly as described in claim 1, wherein the outer casing is formed of an impermeable material and fully encloses the repelling sequence.

3. The repelling magnet assembly as described in claim 2, wherein:

the water pipe is flexible; and the retaining member and the impermeable material of the outer casing are flexible, allowing the repelling sequence to remain in linear alignment with the water pipe when the water pipe undergoes flexing motion.

4. The repelling magnet assembly as described in claim 3, wherein:

each of the plurality of fasteners has a clip portion which projects laterally from the outer casing, the clip portion is adapted to grip the pipe exterior.

5. The repelling magnet assembly as described in claim 2, wherein:

each magnetic component has a magnetic axis extending coaxially with the channel, and the repelling force exerted upon each magnetic component repels the magnetic field of said magnetic component outwardly away from the magnetic axis.

6. The repelling magnet assembly described in claim 5, wherein:

each of the magnetic components comprises two magnetic subcomponents including a first magnetic subcomponent and a second magnetic subcomponent, each of the magnetic subcomponents has a subcomponent first face, a subcomponent second face oriented distally relative to the subcomponent second face, a first magnetic pole oriented with the subcomponent first face, and a second magnetic pole oriented with the subcomponent second face, the subcomponent first face of the first magnetic subcomponent is directly attached to the subcomponent first face of the second magnetic subcomponent, causing the repelling force to be generated between the first magnetic poles of the first magnetic subcomponent and the second magnetic subcomponent; and the second magnetic poles of the first magnetic subcomponent and the second magnetic subcomponent face outwardly away from the subcomponent first faces, and generate the repelling force between each magnetic component and the adjacent magnetic components within the repelling sequence.

7. The repelling magnet assembly described in claim 6, wherein:

the repelling force exerted between the subcomponent first face of the first magnetic subcomponent and the subcomponent first face of the second magnetic subcomponent is overcome by a bonding means which prevents the magnetic subcomponent from separating therebetween.

8. A repelling magnet assembly for use with a water pipe, the water pipe has a pipe exterior, a pipe first end, a pipe second end, and a pipe interior, the pipe interior is adapted to convey water between the pipe first end and the pipe second end, the repelling magnetic assembly comprising:

a plurality of magnetic components, each of the magnetic components projects a magnetic field, and has a magnet first face with a first magnetic pole; and a housing comprising a first portion and a second portion, the first portion and the second portion each have a housing first end, a housing second end distally oriented in relation to the housing first end, a housing inner face extending between the housing first end and the housing second end, and one or more housing interior spaces, each housing interior space encloses one of the magnetic components with the magnet first face oriented outwardly towards the housing inner face, the housing inner face has a channel recess extending longitudinally between the housing first end and the housing second end, the first portion and the second portion are adapted to be placed in an abutting position in which the housing inner face of the first portion abuts against the housing inner face of the second portion and the channel recess of the first portion aligns with the channel recess of the second portion to form a longitudinal retaining channel, the longitudinal retaining channel is adapted to circumferentially grip the pipe exterior and secure the housing to the water pipe, and the abutting position is adapted to cause the magnetic first poles of the magnetic components in the first portion and the second portion to exert a repelling force therebetween, and expose the water within the water pipe to the magnetic fields of the magnetic components.

9. The repelling magnet assembly described in claim 8, wherein the housing further comprises a plurality of fasteners adapted to overcome the repelling force to maintain the first portion and the second portion in the abutting position.

10. The repelling magnet assembly described in claim 9, wherein:

the housing inner face of each of the first portion and the second portion has one or more inner face openings in communication with one of the housing interior spaces, and the first face of each of the magnetic components extends through one of the inner face openings to be coplanar with the housing inner face, and the abutting position places the first face of each of the magnetic components within the first portion in direct contact with the first face of one of the magnetic components within the second portion.

11. The repelling magnet assembly described in claim 10, wherein:

the channel recess bisects the housing inner face to form two contact surfaces, each of the contact surfaces has one of the inner face openings, and the abutting position places the contact surfaces of the first portion in direct contact with the contact surfaces of the second portion.

12. The repelling magnet assembly described in claim 11, wherein:

each of the magnetic components additionally has a magnet second face with a second magnetic pole, and a component body extending between the magnet first face and the magnet second face, the component body forms a connecting curve which places the magnet first face and the magnet second face in coplanar alignment;

the inner face openings of the two contact surfaces of the first portion and the second portion each contain either the magnet first face or the magnet second face of one of the magnetic components; and the abutting position places the magnet second face of the magnetic component of the first portion in direct contact with the magnet second face of the magnetic component of the second portion, causing the magnetic second poles of the first portion and the second portion to generate a repelling force therebetween.

13. The repelling magnet assembly described in claim 12, wherein:

the connecting curves of the magnetic components of the first portion and the second portion circumferentially surround the longitudinal retaining channel when placed in the abutting position.

14. The repelling magnet assembly as described in claim 9, wherein the plurality of fasteners comprise detachable latches configured to selectively place the first portion and the second portion in the abutting position, or release the first portion and the second portion from the abutting position, and the housing is adapted to be detachably secured to the water pipe.

15. The repelling magnet assembly as described in claim 9, further comprising a plurality of additional housings, the additional housings are adapted to be attached to the water pipe to form a housing sequence.

* * * * *